United States Patent
Fendell et al.

(10) Patent No.: US 10,853,454 B2
(45) Date of Patent: *Dec. 1, 2020

(54) PROVIDER PORTAL

(71) Applicant: Palantir Technologies Inc., Palo Alto, CA (US)

(72) Inventors: Sam Fendell, Palo Alto, CA (US); James Thompson, San Francisco, CA (US)

(73) Assignee: Palantir Technologies Inc., Denver, CO (US)

( * ) Notice: Subject to any disclaimer, the term of this patent is extended or adjusted under 35 U.S.C. 154(b) by 345 days.

This patent is subject to a terminal disclaimer.

(21) Appl. No.: 15/826,284

(22) Filed: Nov. 29, 2017

(65) Prior Publication Data

US 2018/0082031 A1 Mar. 22, 2018

Related U.S. Application Data

(63) Continuation of application No. 14/222,364, filed on Mar. 21, 2014, now Pat. No. 9,836,580.

(51) Int. Cl.
*G06Q 40/00* (2012.01)
*G06F 19/00* (2018.01)
(Continued)

(52) U.S. Cl.
CPC ........... *G06F 19/328* (2013.01); *G06Q 40/08* (2013.01); *G06Q 50/22* (2013.01); *G06Q 50/24* (2013.01); *G16H 10/60* (2018.01)

(58) Field of Classification Search
CPC ...... G06F 19/328; G16H 10/60; G06Q 40/08; G06Q 50/22; G06Q 50/24
(Continued)

(56) References Cited

U.S. PATENT DOCUMENTS 5,241,625 A 8/1993 Epard et al.
5,670,987 A 9/1997 Doi et al.
(Continued)

FOREIGN PATENT DOCUMENTS

CA 2556460 A1 * 4/2007 ............ G06Q 40/00
CN 102546446 7/2012
(Continued)

OTHER PUBLICATIONS

Abdullah et al: "Analysis of Effectiveness of Apriori Algorithm in Medical Billing Data Mining", 2008 International Conference on Emerging Technologies IEEE-ICET 2008, Rawalpindi, Pakistan (Year: 2008).*

(Continued)

*Primary Examiner* — Edward J Baird
(74) *Attorney, Agent, or Firm* — Knobbe Martens Olson & Bear LLP

(57) ABSTRACT

Various systems and methods are provided that graphically allow health insurance company personnel to identify patient diagnoses that are not accounted for by the health insurance company. Furthermore, the various systems and methods graphically allow health insurance company personnel to identify patients that have not submitted claims for documented ailments or conditions. Thus, the health insurance company may be able to improve its chances of receiving transfer payments from other health insurance companies and/or receiving higher star ratings.

20 Claims, 23 Drawing Sheets

(51) Int. Cl.
*G06Q 40/08* (2012.01)
*G06Q 50/24* (2012.01)
*G06Q 50/22* (2018.01)
*G16H 10/60* (2018.01)

(58) Field of Classification Search
USPC .................................................. 705/4, 35–40
See application file for complete search history.

(56) References Cited

U.S. PATENT DOCUMENTS

| | | | |
|---|---|---|---|
| 5,819,226 A | 10/1998 | Gopinathan et al. |
| 5,826,021 A | 10/1998 | Mastors et al. |
| 5,832,218 A | 11/1998 | Gibbs et al. |
| 5,845,300 A | 12/1998 | Comer |
| 5,878,434 A | 3/1999 | Draper et al. |
| 5,892,900 A | 4/1999 | Ginter et al. |
| 5,893,072 A | 4/1999 | Zizzamia |
| 5,897,636 A | 4/1999 | Kaeser |
| 5,966,706 A | 10/1999 | Biliris et al. |
| 5,999,911 A | 12/1999 | Berg et al. |
| 6,006,242 A | 12/1999 | Poole et al. |
| 6,057,757 A | 5/2000 | Arrowsmith et al. |
| 6,065,026 A | 5/2000 | Cornelia et al. |
| 6,094,643 A | 7/2000 | Anderson et al. |
| 6,134,582 A | 10/2000 | Kennedy |
| 6,161,098 A | 12/2000 | Wallman |
| 6,219,053 B1 | 4/2001 | Tachibana et al. |
| 6,232,971 B1 | 5/2001 | Haynes |
| 6,237,138 B1 | 5/2001 | Hameluck et al. |
| 6,243,706 B1 | 6/2001 | Moreau et al. |
| 6,243,717 B1 | 6/2001 | Gordon et al. |
| 6,279,018 B1 | 8/2001 | Kudrolli et al. |
| 6,341,310 B1 | 1/2002 | Leshem et al. |
| 6,369,835 B1 | 4/2002 | Lin |
| 6,370,538 B1 | 4/2002 | Lamping et al. |
| 6,430,305 B1 | 8/2002 | Decker |
| 6,463,404 B1 | 10/2002 | Appleby |
| 6,505,196 B2 | 1/2003 | Drucker et al. |
| 6,519,627 B1 | 2/2003 | Dan et al. |
| 6,523,019 B1 | 2/2003 | Borthwick |
| 6,549,944 B1 | 4/2003 | Weinberg et al. |
| 6,714,936 B1 | 3/2004 | Nevin, III |
| 6,820,135 B1 | 11/2004 | Dingman |
| 6,839,745 B1 | 1/2005 | Dingari et al. |
| 6,944,821 B1 | 9/2005 | Bates et al. |
| 6,978,419 B1 | 12/2005 | Kantrowitz |
| 6,980,984 B1 | 12/2005 | Huffman et al. |
| 7,058,648 B1 | 6/2006 | Lightfoot et al. |
| 7,086,028 B1 | 8/2006 | Davis et al. |
| 7,089,541 B2 | 8/2006 | Ungar |
| 7,139,800 B2 | 11/2006 | Bellotti et al. |
| 7,168,039 B2 | 1/2007 | Bertram |
| 7,171,427 B2 | 1/2007 | Witowski et al. |
| 7,174,377 B2 | 2/2007 | Bernard et al. |
| 7,213,030 B1 | 5/2007 | Jenkins |
| 7,254,555 B2 * | 8/2007 | Field .................... G06Q 40/06 705/36 R |
| 7,278,105 B1 | 10/2007 | Kitts |
| 7,379,903 B2 | 5/2008 | Caballero et al. |
| 7,383,239 B2 | 6/2008 | Bonissone |
| 7,392,254 B1 | 6/2008 | Jenkins |
| 7,403,942 B1 | 7/2008 | Bayliss |
| 7,418,431 B1 | 8/2008 | Nies et al. |
| 7,426,654 B2 | 9/2008 | Adams et al. |
| 7,441,182 B2 | 10/2008 | Beilinson et al. |
| 7,454,466 B2 | 11/2008 | Bellotti et al. |
| 7,461,158 B2 | 12/2008 | Rider et al. |
| 7,467,375 B2 | 12/2008 | Tondreau et al. |
| 7,525,422 B2 | 4/2009 | Bishop et al. |
| 7,617,232 B2 | 11/2009 | Gabbert et al. |
| 7,627,489 B2 | 12/2009 | Schaeffer et al. |
| 7,627,812 B2 | 12/2009 | Chamberlain et al. |
| 7,634,717 B2 | 12/2009 | Chamberlain et al. |
| 7,703,021 B1 | 4/2010 | Flam |
| 7,716,077 B1 | 5/2010 | Mikurak |
| 7,725,547 B2 | 5/2010 | Albertson et al. |
| 7,756,843 B1 | 7/2010 | Palmer |
| 7,757,220 B2 | 7/2010 | Griffith et al. |
| 7,765,489 B1 | 7/2010 | Shah |
| 7,770,100 B2 | 8/2010 | Chamberlain et al. |
| 7,813,937 B1 | 10/2010 | Pathria et al. |
| 7,818,658 B2 | 10/2010 | Chen |
| 7,827,045 B2 | 11/2010 | Madill et al. |
| 7,877,421 B2 | 1/2011 | Berger et al. |
| 7,880,921 B2 | 2/2011 | Dattilo et al. |
| 7,899,796 B1 | 3/2011 | Borthwick et al. |
| 7,912,842 B1 | 3/2011 | Bayliss |
| 7,917,376 B2 | 3/2011 | Bellin et al. |
| 7,941,321 B2 | 5/2011 | Greenstein et al. |
| 7,941,336 B1 | 5/2011 | Robin-Jan |
| 7,958,147 B1 | 6/2011 | Turner et al. |
| 7,962,495 B2 | 6/2011 | Jain et al. |
| 7,962,848 B2 | 6/2011 | Bertram |
| 7,966,199 B1 | 6/2011 | Frasher |
| 8,001,465 B2 | 8/2011 | Kudrolli et al. |
| 8,001,482 B2 | 8/2011 | Bhattiprolu et al. |
| 8,010,507 B2 | 8/2011 | Poston et al. |
| 8,015,487 B2 | 9/2011 | Roy et al. |
| 8,036,971 B2 | 10/2011 | Aymeloglu et al. |
| 8,046,283 B2 | 10/2011 | Burns |
| 8,054,756 B2 | 11/2011 | Chand et al. |
| 8,073,857 B2 | 12/2011 | Sreekanth |
| 8,117,022 B2 | 2/2012 | Linker |
| 8,126,848 B2 | 2/2012 | Wagner |
| 8,214,232 B2 | 7/2012 | Tyler et al. |
| 8,214,490 B1 | 7/2012 | Vos et al. |
| 8,225,201 B2 | 7/2012 | Michael |
| 8,229,902 B2 | 7/2012 | Vishniac et al. |
| 8,230,333 B2 | 7/2012 | Decherd et al. |
| 8,290,838 B1 | 10/2012 | Thakur et al. |
| 8,301,464 B1 | 10/2012 | Cave et al. |
| 8,302,855 B2 | 11/2012 | Ma et al. |
| 8,364,642 B1 | 1/2013 | Garrod |
| 8,417,715 B1 | 4/2013 | Bruckhaus et al. |
| 8,429,527 B1 | 4/2013 | Arbogast |
| 8,447,722 B1 | 5/2013 | Ahuja et al. |
| 8,473,454 B2 | 6/2013 | Evanitsky et al. |
| 8,484,115 B2 | 7/2013 | Aymeloglu et al. |
| 8,489,623 B2 | 7/2013 | Jain et al. |
| 8,489,641 B1 | 7/2013 | Seefeld et al. |
| 8,514,082 B2 | 8/2013 | Cova et al. |
| 8,515,912 B2 | 8/2013 | Garrod et al. |
| 8,527,461 B2 | 9/2013 | Ducott, III et al. |
| 8,538,827 B1 | 9/2013 | Dryer et al. |
| 8,554,579 B2 | 10/2013 | Tribble et al. |
| 8,554,719 B2 | 10/2013 | McGrew |
| 8,577,911 B1 | 11/2013 | Stepinski et al. |
| 8,578,500 B2 | 11/2013 | Long |
| 8,589,273 B2 | 11/2013 | Creeden et al. |
| 8,600,872 B1 | 12/2013 | Yan |
| 8,601,326 B1 | 12/2013 | Kirn |
| 8,620,641 B2 | 12/2013 | Farnsworth et al. |
| 8,639,522 B2 | 1/2014 | Pathria et al. |
| 8,639,552 B1 | 1/2014 | Chen et al. |
| 8,655,687 B2 | 2/2014 | Zizzamia |
| 8,666,861 B2 | 3/2014 | Li et al. |
| 8,682,696 B1 | 3/2014 | Shanmugam |
| 8,688,573 B1 | 4/2014 | Ruknoic et al. |
| 8,689,108 B1 | 4/2014 | Duffield et al. |
| 8,713,467 B1 | 4/2014 | Goldenberg et al. |
| 8,732,574 B2 | 5/2014 | Burr et al. |
| 8,744,890 B1 | 6/2014 | Bernier |
| 8,798,354 B1 | 8/2014 | Bunzel et al. |
| 8,799,313 B2 | 8/2014 | Satlow |
| 8,812,960 B1 | 8/2014 | Sun et al. |
| 8,903,717 B2 | 12/2014 | Elliot |
| 8,924,388 B2 | 12/2014 | Elliot et al. |
| 8,924,389 B2 | 12/2014 | Elliot et al. |
| 8,938,686 B1 | 1/2015 | Erenrich et al. |
| 8,949,164 B1 | 2/2015 | Mohler |
| 8,984,390 B2 | 3/2015 | Aymeloglu et al. |
| 9,032,531 B1 | 5/2015 | Scorvo et al. |
| 9,058,315 B2 | 6/2015 | Burr et al. |

(56) References Cited

U.S. PATENT DOCUMENTS

| | | |
|---|---|---|
| 9,100,428 B1 | 8/2015 | Visbal |
| 9,105,000 B1 | 8/2015 | White et al. |
| 9,129,219 B1 | 9/2015 | Robertson et al. |
| 9,418,337 B1 | 8/2016 | Elser et al. |
| 9,836,580 B2 | 12/2017 | Fendell et al. |
| 2001/0021936 A1 | 9/2001 | Bertram |
| 2001/0027424 A1 | 10/2001 | Torigoe |
| 2002/0032677 A1 | 3/2002 | Morgenthaler et al. |
| 2002/0035590 A1 | 3/2002 | Eibach et al. |
| 2002/0065708 A1 | 5/2002 | Senay et al. |
| 2002/0095360 A1 | 7/2002 | Joao |
| 2002/0095658 A1 | 7/2002 | Shulman |
| 2002/0103705 A1 | 8/2002 | Brady |
| 2002/0130907 A1 | 9/2002 | Chi et al. |
| 2002/0147805 A1 | 10/2002 | Leshem et al. |
| 2002/0174201 A1 | 11/2002 | Ramer et al. |
| 2003/0033347 A1 | 2/2003 | Bolle et al. |
| 2003/0036927 A1 | 2/2003 | Bowen |
| 2003/0093401 A1 | 5/2003 | Czahkowski et al. |
| 2003/0093755 A1 | 5/2003 | O'Carroll |
| 2003/0105759 A1 | 6/2003 | Bess et al. |
| 2003/0115481 A1 | 6/2003 | Baird et al. |
| 2003/0126102 A1 | 7/2003 | Borthwick |
| 2003/0163352 A1 | 8/2003 | Surpin et al. |
| 2003/0177112 A1 | 9/2003 | Gardner |
| 2003/0182313 A1 | 9/2003 | Federwisch et al. |
| 2003/0200217 A1 | 10/2003 | Ackerman |
| 2003/0208465 A1* | 11/2003 | Yurko .................. G16H 10/60 |
| 2003/0212718 A1 | 11/2003 | Tester |
| 2004/0003009 A1 | 1/2004 | Wilmot |
| 2004/0006523 A1 | 1/2004 | Coker |
| 2004/0034570 A1 | 2/2004 | Davis |
| 2004/0044648 A1 | 3/2004 | Anfindsen et al. |
| 2004/0083466 A1 | 4/2004 | Dapp et al. |
| 2004/0085318 A1 | 5/2004 | Hassler et al. |
| 2004/0088177 A1 | 5/2004 | Travis et al. |
| 2004/0095349 A1 | 5/2004 | Bito et al. |
| 2004/0111480 A1 | 6/2004 | Yue |
| 2004/0117387 A1 | 6/2004 | Civetta et al. |
| 2004/0126840 A1 | 7/2004 | Cheng et al. |
| 2004/0153418 A1 | 8/2004 | Hanweck |
| 2004/0153451 A1 | 8/2004 | Phillips et al. |
| 2004/0181554 A1 | 9/2004 | Heckerman et al. |
| 2004/0205492 A1 | 10/2004 | Newsome |
| 2004/0210763 A1 | 10/2004 | Jonas |
| 2004/0236688 A1 | 11/2004 | Bozeman |
| 2005/0010472 A1 | 1/2005 | Quatse et al. |
| 2005/0028094 A1 | 2/2005 | Allyn |
| 2005/0039116 A1 | 2/2005 | Slack-Smith |
| 2005/0060184 A1* | 3/2005 | Wahlbin .................. G06Q 40/02 705/2 |
| 2005/0086207 A1 | 4/2005 | Heuer et al. |
| 2005/0091186 A1 | 4/2005 | Elish |
| 2005/0097441 A1 | 5/2005 | Herbach et al. |
| 2005/0108063 A1 | 5/2005 | Madill et al. |
| 2005/0125715 A1 | 6/2005 | Di Franco et al. |
| 2005/0131935 A1 | 6/2005 | O'Leary et al. |
| 2005/0133588 A1 | 6/2005 | Williams |
| 2005/0149455 A1 | 7/2005 | Bruesewitz et al. |
| 2005/0149527 A1 | 7/2005 | Berlin |
| 2005/0154628 A1 | 7/2005 | Eckart et al. |
| 2005/0154769 A1 | 7/2005 | Eckart et al. |
| 2005/0180330 A1 | 8/2005 | Shapiro |
| 2005/0182654 A1 | 8/2005 | Abolfathi et al. |
| 2005/0228699 A1* | 10/2005 | Samuels .................. G06Q 50/22 705/4 |
| 2005/0262512 A1 | 11/2005 | Schmidt et al. |
| 2006/0010130 A1 | 1/2006 | Leff et al. |
| 2006/0026120 A1 | 2/2006 | Carolan et al. |
| 2006/0026170 A1 | 2/2006 | Kreitler et al. |
| 2006/0026561 A1 | 2/2006 | Bauman et al. |
| 2006/0031779 A1 | 2/2006 | Theurer et al. |
| 2006/0045470 A1 | 3/2006 | Poslinski et al. |
| 2006/0053097 A1 | 3/2006 | King et al. |
| 2006/0053170 A1 | 3/2006 | Hill et al. |
| 2006/0059423 A1 | 3/2006 | Lehmann et al. |
| 2006/0074866 A1 | 4/2006 | Chamberlain et al. |
| 2006/0080139 A1 | 4/2006 | Mainzer |
| 2006/0080316 A1 | 4/2006 | Gilmore et al. |
| 2006/0080619 A1 | 4/2006 | Carlson et al. |
| 2006/0129746 A1 | 6/2006 | Porter |
| 2006/0136513 A1 | 6/2006 | Ngo et al. |
| 2006/0142949 A1 | 6/2006 | Helt |
| 2006/0143034 A1 | 6/2006 | Rothermel |
| 2006/0143075 A1 | 6/2006 | Carr et al. |
| 2006/0143079 A1 | 6/2006 | Basak et al. |
| 2006/0149596 A1 | 7/2006 | Surpin et al. |
| 2006/0178915 A1 | 8/2006 | Chao |
| 2006/0218206 A1 | 9/2006 | Bourbonnais et al. |
| 2006/0218491 A1 | 9/2006 | Grossman et al. |
| 2006/0241974 A1 | 10/2006 | Chao et al. |
| 2006/0253502 A1 | 11/2006 | Raman et al. |
| 2006/0265417 A1 | 11/2006 | Amato et al. |
| 2006/0277460 A1 | 12/2006 | Forstall et al. |
| 2007/0000999 A1 | 1/2007 | Kubo et al. |
| 2007/0011304 A1 | 1/2007 | Error |
| 2007/0038646 A1 | 2/2007 | Thota |
| 2007/0043686 A1 | 2/2007 | Teng et al. |
| 2007/0061259 A1 | 3/2007 | Zoldi et al. |
| 2007/0061752 A1 | 3/2007 | Cory |
| 2007/0067285 A1 | 3/2007 | Blume |
| 2007/0106582 A1 | 5/2007 | Baker et al. |
| 2007/0113164 A1 | 5/2007 | Hansen et al. |
| 2007/0136095 A1 | 6/2007 | Weinstein |
| 2007/0150801 A1 | 6/2007 | Chidlovskii et al. |
| 2007/0156673 A1 | 7/2007 | Maga |
| 2007/0168871 A1 | 7/2007 | Jenkins |
| 2007/0178501 A1 | 8/2007 | Rabinowitz et al. |
| 2007/0185867 A1 | 8/2007 | Maga |
| 2007/0192143 A1 | 8/2007 | Krishnan et al. |
| 2007/0233756 A1 | 10/2007 | D'Souza et al. |
| 2007/0239606 A1 | 10/2007 | Eisen |
| 2007/0245339 A1 | 10/2007 | Bauman et al. |
| 2007/0266336 A1 | 11/2007 | Nojima et al. |
| 2007/0271317 A1 | 11/2007 | Carmel |
| 2007/0284433 A1 | 12/2007 | Domenica et al. |
| 2007/0295797 A1 | 12/2007 | Herman et al. |
| 2007/0299697 A1 | 12/2007 | Friedlander et al. |
| 2008/0005063 A1 | 1/2008 | Seeds |
| 2008/0016155 A1 | 1/2008 | Khalatian |
| 2008/0046481 A1 | 2/2008 | Gould et al. |
| 2008/0069081 A1 | 3/2008 | Chand et al. |
| 2008/0077597 A1 | 3/2008 | Butler |
| 2008/0077642 A1 | 3/2008 | Carbone et al. |
| 2008/0091693 A1 | 4/2008 | Murthy |
| 2008/0103798 A1 | 5/2008 | Domenikos et al. |
| 2008/0103996 A1 | 5/2008 | Forman et al. |
| 2008/0109714 A1 | 5/2008 | Kumar et al. |
| 2008/0126344 A1 | 5/2008 | Hoffman et al. |
| 2008/0126951 A1 | 5/2008 | Sood et al. |
| 2008/0140387 A1 | 6/2008 | Linker |
| 2008/0140576 A1 | 6/2008 | Lewis et al. |
| 2008/0155440 A1 | 6/2008 | Trevor et al. |
| 2008/0172257 A1 | 7/2008 | Bisker et al. |
| 2008/0172607 A1 | 7/2008 | Baer |
| 2008/0195417 A1 | 8/2008 | Surpin et al. |
| 2008/0195421 A1 | 8/2008 | Ludwig et al. |
| 2008/0195672 A1 | 8/2008 | Hamel et al. |
| 2008/0222038 A1 | 9/2008 | Eden et al. |
| 2008/0222295 A1 | 9/2008 | Robinson et al. |
| 2008/0228467 A1 | 9/2008 | Womack et al. |
| 2008/0235199 A1 | 9/2008 | Li et al. |
| 2008/0243711 A1 | 10/2008 | Aymeloglu et al. |
| 2008/0249820 A1 | 10/2008 | Pathria |
| 2008/0255973 A1 | 10/2008 | El Wade et al. |
| 2008/0263468 A1 | 10/2008 | Cappione et al. |
| 2008/0267386 A1 | 10/2008 | Cooper |
| 2008/0270316 A1 | 10/2008 | Guidotti et al. |
| 2008/0270438 A1 | 10/2008 | Aronson et al. |
| 2008/0281580 A1 | 11/2008 | Zabokritski |
| 2008/0281819 A1 | 11/2008 | Tenenbaum et al. |
| 2008/0301042 A1 | 12/2008 | Patzer |
| 2008/0313132 A1 | 12/2008 | Hao et al. |
| 2008/0313243 A1 | 12/2008 | Poston et al. |

(56) References Cited

U.S. PATENT DOCUMENTS

| | | |
|---|---|---|
| 2009/0012813 A1* | 1/2009 | Berzansky ............ G06Q 10/06 705/2 |
| 2009/0018996 A1 | 1/2009 | Hunt et al. |
| 2009/0031401 A1 | 1/2009 | Cudich et al. |
| 2009/0043801 A1 | 2/2009 | LeClair |
| 2009/0055208 A1 | 2/2009 | Kaiser |
| 2009/0055487 A1 | 2/2009 | Moraes et al. |
| 2009/0070162 A1 | 3/2009 | Leonelli et al. |
| 2009/0076845 A1 | 3/2009 | Bellin et al. |
| 2009/0089651 A1 | 4/2009 | Herberger et al. |
| 2009/0094166 A1 | 4/2009 | Aymeloglu et al. |
| 2009/0106178 A1 | 4/2009 | Chu |
| 2009/0106242 A1 | 4/2009 | McGrew |
| 2009/0112678 A1 | 4/2009 | Luzardo |
| 2009/0112745 A1 | 4/2009 | Stefanescu |
| 2009/0125359 A1 | 5/2009 | Knapic |
| 2009/0125459 A1 | 5/2009 | Norton et al. |
| 2009/0132953 A1 | 5/2009 | Reed et al. |
| 2009/0150868 A1 | 6/2009 | Chakra et al. |
| 2009/0164387 A1 | 6/2009 | Armstrong et al. |
| 2009/0164934 A1 | 6/2009 | Bhattiprolu et al. |
| 2009/0177492 A1 | 7/2009 | Hasan et al. |
| 2009/0187546 A1 | 7/2009 | Whyte et al. |
| 2009/0187548 A1 | 7/2009 | Ji et al. |
| 2009/0198518 A1 | 8/2009 | McKenzie et al. |
| 2009/0199106 A1 | 8/2009 | Jonsson et al. |
| 2009/0216562 A1 | 8/2009 | Faulkner et al. |
| 2009/0222287 A1 | 9/2009 | Legorreta et al. |
| 2009/0228365 A1 | 9/2009 | Tomchek et al. |
| 2009/0240529 A1 | 9/2009 | Chess et al. |
| 2009/0248757 A1 | 10/2009 | Havewala et al. |
| 2009/0249244 A1 | 10/2009 | Robinson et al. |
| 2009/0271343 A1 | 10/2009 | Vaiciulis et al. |
| 2009/0281839 A1 | 11/2009 | Lynn et al. |
| 2009/0287470 A1 | 11/2009 | Farnsworth et al. |
| 2009/0299830 A1 | 12/2009 | West et al. |
| 2009/0307049 A1 | 12/2009 | Elliott et al. |
| 2009/0313311 A1 | 12/2009 | Hoffmann et al. |
| 2009/0313463 A1 | 12/2009 | Pang et al. |
| 2009/0319418 A1 | 12/2009 | Herz |
| 2009/0319891 A1 | 12/2009 | MacKinlay |
| 2010/0030722 A1 | 2/2010 | Goodson et al. |
| 2010/0031141 A1 | 2/2010 | Summers et al. |
| 2010/0042922 A1 | 2/2010 | Bradateanu et al. |
| 2010/0057622 A1 | 3/2010 | Faith et al. |
| 2010/0070531 A1 | 3/2010 | Aymeloglu et al. |
| 2010/0070842 A1 | 3/2010 | Aymeloglu et al. |
| 2010/0070844 A1 | 3/2010 | Aymeloglu et al. |
| 2010/0070897 A1 | 3/2010 | Aymeloglu et al. |
| 2010/0082369 A1 | 4/2010 | Prenelus et al. |
| 2010/0082541 A1 | 4/2010 | Kottomtharayil |
| 2010/0082671 A1 | 4/2010 | Li et al. |
| 2010/0094765 A1 | 4/2010 | Nandy |
| 2010/0098318 A1 | 4/2010 | Anderson |
| 2010/0114817 A1 | 5/2010 | Broeder et al. |
| 2010/0114887 A1 | 5/2010 | Conway et al. |
| 2010/0122152 A1 | 5/2010 | Chamberlain et al. |
| 2010/0131502 A1 | 5/2010 | Fordham |
| 2010/0145909 A1 | 6/2010 | Ngo |
| 2010/0161735 A1 | 6/2010 | Sharma |
| 2010/0169192 A1 | 7/2010 | Zoldi et al. |
| 2010/0191563 A1 | 7/2010 | Schlaifer et al. |
| 2010/0204983 A1 | 8/2010 | Chung et al. |
| 2010/0223260 A1 | 9/2010 | Wu |
| 2010/0235915 A1 | 9/2010 | Memon et al. |
| 2010/0262688 A1 | 10/2010 | Hussain et al. |
| 2010/0280851 A1 | 11/2010 | Merkin |
| 2010/0293174 A1 | 11/2010 | Bennett et al. |
| 2010/0306285 A1 | 12/2010 | Shah et al. |
| 2010/0306713 A1 | 12/2010 | Geisner et al. |
| 2010/0312837 A1 | 12/2010 | Bodapati et al. |
| 2010/0313239 A1 | 12/2010 | Chakra et al. |
| 2010/0324929 A1 | 12/2010 | Petrasich et al. |
| 2010/0325581 A1 | 12/2010 | Finkelstein et al. |
| 2011/0004626 A1 | 1/2011 | Naeymi-Rad et al. |
| 2011/0047159 A1 | 2/2011 | Baid et al. |
| 2011/0055074 A1 | 3/2011 | Chen et al. |
| 2011/0060753 A1 | 3/2011 | Shaked et al. |
| 2011/0061013 A1 | 3/2011 | Bilicki et al. |
| 2011/0066497 A1 | 3/2011 | Gopinath et al. |
| 2011/0078173 A1 | 3/2011 | Seligmann et al. |
| 2011/0093327 A1 | 4/2011 | Fordyce, III et al. |
| 2011/0099133 A1 | 4/2011 | Chang et al. |
| 2011/0099628 A1 | 4/2011 | Lanxner et al. |
| 2011/0131122 A1 | 6/2011 | Griffin et al. |
| 2011/0153384 A1 | 6/2011 | Horne et al. |
| 2011/0161409 A1 | 6/2011 | Nair |
| 2011/0167105 A1 | 7/2011 | Ramakrishnan et al. |
| 2011/0173093 A1 | 7/2011 | Psota et al. |
| 2011/0179048 A1 | 7/2011 | Satlow |
| 2011/0208565 A1 | 8/2011 | Ross et al. |
| 2011/0208724 A1 | 8/2011 | Jones et al. |
| 2011/0208822 A1 | 8/2011 | Rathod |
| 2011/0213655 A1 | 9/2011 | Henkin |
| 2011/0218955 A1 | 9/2011 | Tang |
| 2011/0225482 A1 | 9/2011 | Chan et al. |
| 2011/0225586 A1 | 9/2011 | Bentley et al. |
| 2011/0231305 A1 | 9/2011 | Winters |
| 2011/0246229 A1 | 10/2011 | Pacha |
| 2011/0252282 A1 | 10/2011 | Meek et al. |
| 2011/0258216 A1 | 10/2011 | Supakkul et al. |
| 2011/0270604 A1 | 11/2011 | Qi et al. |
| 2011/0270834 A1 | 11/2011 | Sokolan et al. |
| 2011/0289397 A1 | 11/2011 | Eastmond et al. |
| 2011/0291851 A1 | 12/2011 | Whisenant |
| 2011/0295649 A1 | 12/2011 | Fine |
| 2011/0307382 A1 | 12/2011 | Siegel et al. |
| 2011/0310005 A1 | 12/2011 | Chen et al. |
| 2011/0314007 A1 | 12/2011 | Dassa et al. |
| 2011/0314024 A1 | 12/2011 | Chang et al. |
| 2012/0004894 A1 | 1/2012 | Butler |
| 2012/0011238 A1 | 1/2012 | Rathod |
| 2012/0011245 A1 | 1/2012 | Gillette et al. |
| 2012/0013684 A1 | 1/2012 | Robertson et al. |
| 2012/0019559 A1 | 1/2012 | Siler et al. |
| 2012/0022945 A1 | 1/2012 | Falkenborg et al. |
| 2012/0036434 A1 | 2/2012 | Oberstein |
| 2012/0054284 A1 | 3/2012 | Rakshit |
| 2012/0059853 A1 | 3/2012 | Jagota |
| 2012/0065987 A1 | 3/2012 | Farooq et al. |
| 2012/0066166 A1 | 3/2012 | Curbera et al. |
| 2012/0078595 A1 | 3/2012 | Balandin et al. |
| 2012/0079363 A1 | 3/2012 | Folting et al. |
| 2012/0084117 A1 | 4/2012 | Tavares et al. |
| 2012/0084184 A1 | 4/2012 | Raleigh |
| 2012/0084287 A1 | 4/2012 | Lakshminarayan et al. |
| 2012/0096384 A1* | 4/2012 | Albert ................... G06Q 40/06 715/772 |
| 2012/0131512 A1 | 5/2012 | Takeuchi et al. |
| 2012/0144335 A1 | 6/2012 | Abeln et al. |
| 2012/0158585 A1 | 6/2012 | Ganti |
| 2012/0159362 A1 | 6/2012 | Brown et al. |
| 2012/0173381 A1 | 7/2012 | Smith |
| 2012/0188252 A1 | 7/2012 | Law |
| 2012/0191446 A1 | 7/2012 | Binsztok et al. |
| 2012/0196558 A1 | 8/2012 | Reich et al. |
| 2012/0197657 A1 | 8/2012 | Prodanovic |
| 2012/0197660 A1 | 8/2012 | Prodanovic |
| 2012/0215784 A1 | 8/2012 | King et al. |
| 2012/0221553 A1 | 8/2012 | Wittmer et al. |
| 2012/0221580 A1 | 8/2012 | Barney |
| 2012/0226523 A1 | 9/2012 | Weiss |
| 2012/0226590 A1 | 9/2012 | Love et al. |
| 2012/0245976 A1 | 9/2012 | Kumar et al. |
| 2012/0246148 A1 | 9/2012 | Dror |
| 2012/0278249 A1 | 11/2012 | Duggal et al. |
| 2012/0310661 A1 | 12/2012 | Greene |
| 2012/0323888 A1 | 12/2012 | Osann, Jr. |
| 2012/0330973 A1 | 12/2012 | Ghuneim et al. |
| 2013/0006655 A1 | 1/2013 | Van Arkel et al. |
| 2013/0006668 A1 | 1/2013 | Van Arkel et al. |
| 2013/0016106 A1 | 1/2013 | Yip et al. |
| 2013/0046842 A1 | 2/2013 | Muntz et al. |
| 2013/0054306 A1 | 2/2013 | Bhalla |

(56) References Cited

U.S. PATENT DOCUMENTS

| | | |
|---|---|---|
| 2013/0057551 A1 | 3/2013 | Ebert et al. |
| 2013/0061169 A1 | 3/2013 | Pearcy et al. |
| 2013/0073377 A1 | 3/2013 | Heath |
| 2013/0096968 A1 | 4/2013 | Van Pelt et al. |
| 2013/0096988 A1 | 4/2013 | Grossman et al. |
| 2013/0097130 A1 | 4/2013 | Bingol et al. |
| 2013/0097482 A1 | 4/2013 | Marantz et al. |
| 2013/0110746 A1 | 5/2013 | Ahn |
| 2013/0117081 A1 | 5/2013 | Wilkins et al. |
| 2013/0124193 A1 | 5/2013 | Holmberg |
| 2013/0132348 A1 | 5/2013 | Garrod |
| 2013/0151453 A1 | 6/2013 | Bhanot et al. |
| 2013/0166348 A1 | 6/2013 | Scotto |
| 2013/0166480 A1 | 6/2013 | Popescu et al. |
| 2013/0185245 A1 | 7/2013 | Anderson |
| 2013/0185307 A1 | 7/2013 | El-Yaniv et al. |
| 2013/0224696 A1 | 8/2013 | Wolfe et al. |
| 2013/0226318 A1 | 8/2013 | Procyk |
| 2013/0226944 A1 | 8/2013 | Baid et al. |
| 2013/0238616 A1 | 9/2013 | Rose et al. |
| 2013/0238664 A1 | 9/2013 | Hsu et al. |
| 2013/0246170 A1 | 9/2013 | Gross et al. |
| 2013/0246537 A1 | 9/2013 | Gaddala |
| 2013/0246597 A1 | 9/2013 | Iizawa et al. |
| 2013/0262328 A1 | 10/2013 | Federgreen |
| 2013/0262527 A1 | 10/2013 | Hunter et al. |
| 2013/0263019 A1 | 10/2013 | Castellanos et al. |
| 2013/0276799 A1 | 10/2013 | Davidson |
| 2013/0282696 A1 | 10/2013 | John et al. |
| 2013/0290011 A1 | 10/2013 | Lynn et al. |
| 2013/0290825 A1 | 10/2013 | Arndt et al. |
| 2013/0297619 A1 | 11/2013 | Chandrasekaran et al. |
| 2013/0304770 A1 | 11/2013 | Boero et al. |
| 2013/0325826 A1 | 12/2013 | Agarwal et al. |
| 2014/0006404 A1 | 1/2014 | McGrew et al. |
| 2014/0012724 A1 | 1/2014 | O'Leary et al. |
| 2014/0012796 A1 | 1/2014 | Petersen et al. |
| 2014/0019936 A1 | 1/2014 | Cohanoff |
| 2014/0032506 A1 | 1/2014 | Hoey et al. |
| 2014/0033010 A1 | 1/2014 | Richardt et al. |
| 2014/0040371 A1 | 2/2014 | Gurevich et al. |
| 2014/0052466 A1 | 2/2014 | DeVille et al. |
| 2014/0058754 A1 | 2/2014 | Wild |
| 2014/0058763 A1 | 2/2014 | Zizzamia et al. |
| 2014/0058914 A1 | 2/2014 | Song et al. |
| 2014/0068487 A1 | 3/2014 | Steiger et al. |
| 2014/0081652 A1 | 3/2014 | Klindworth |
| 2014/0095363 A1 | 4/2014 | Caldwell |
| 2014/0095509 A1 | 4/2014 | Patton |
| 2014/0108074 A1 | 4/2014 | Miller et al. |
| 2014/0108380 A1 | 4/2014 | Gotz et al. |
| 2014/0108985 A1 | 4/2014 | Scott et al. |
| 2014/0123279 A1 | 5/2014 | Bishop et al. |
| 2014/0129936 A1 | 5/2014 | Richards et al. |
| 2014/0136237 A1 | 5/2014 | Anderson et al. |
| 2014/0136285 A1 | 5/2014 | Carvalho |
| 2014/0143009 A1 | 5/2014 | Brice et al. |
| 2014/0149130 A1 | 5/2014 | Getchius |
| 2014/0156527 A1 | 6/2014 | Grigg et al. |
| 2014/0157172 A1 | 6/2014 | Peery et al. |
| 2014/0164502 A1 | 6/2014 | Khodorenko et al. |
| 2014/0189536 A1 | 7/2014 | Lange et al. |
| 2014/0195515 A1 | 7/2014 | Baker et al. |
| 2014/0214579 A1 | 7/2014 | Shen et al. |
| 2014/0222521 A1 | 8/2014 | Chait |
| 2014/0222752 A1 | 8/2014 | Isman et al. |
| 2014/0222793 A1 | 8/2014 | Sadkin et al. |
| 2014/0229554 A1 | 8/2014 | Grunin et al. |
| 2014/0244284 A1 | 8/2014 | Smith |
| 2014/0278479 A1 | 9/2014 | Wang et al. |
| 2014/0282177 A1 | 9/2014 | Wang et al. |
| 2014/0344230 A1 | 11/2014 | Krause et al. |
| 2014/0358789 A1 | 12/2014 | Boding et al. |
| 2014/0358829 A1 | 12/2014 | Hurwitz |
| 2014/0366132 A1 | 12/2014 | Stiansen et al. |
| 2015/0012509 A1 | 1/2015 | Kirn |
| 2015/0046481 A1 | 2/2015 | Elliot |
| 2015/0073929 A1 | 3/2015 | Psota et al. |
| 2015/0073954 A1 | 3/2015 | Braff |
| 2015/0085997 A1 | 3/2015 | Biage et al. |
| 2015/0095773 A1 | 4/2015 | Gonsalves et al. |
| 2015/0100897 A1 | 4/2015 | Sun et al. |
| 2015/0106379 A1 | 4/2015 | Elliot et al. |
| 2015/0134512 A1 | 5/2015 | Mueller |
| 2015/0135256 A1 | 5/2015 | Hoy et al. |
| 2015/0161611 A1 | 6/2015 | Duke et al. |
| 2015/0186821 A1 | 7/2015 | Wang et al. |
| 2015/0187036 A1 | 7/2015 | Wang et al. |
| 2015/0188872 A1 | 7/2015 | White |
| 2015/0235334 A1 | 8/2015 | Wang et al. |
| 2015/0254220 A1 | 9/2015 | Burr et al. |
| 2015/0269316 A1 | 9/2015 | Hussam |
| 2015/0269334 A1 | 9/2015 | Fendell et al. |
| 2015/0338233 A1 | 11/2015 | Cervelli et al. |
| 2015/0379413 A1 | 12/2015 | Robertson et al. |
| 2016/0004764 A1 | 1/2016 | Chakerian et al. |
| 2016/0034578 A1 | 2/2016 | Wang et al. |

FOREIGN PATENT DOCUMENTS

| | | |
|---|---|---|
| CN | 103167093 | 6/2013 |
| CN | 102054015 | 5/2014 |
| DE | 102014103476 | 9/2014 |
| DE | 102014204827 | 9/2014 |
| DE | 102014204830 | 9/2014 |
| DE | 102014204834 | 9/2014 |
| DE | 102014213036 | 1/2015 |
| EP | 1672527 | 6/2006 |
| EP | 2487610 | 8/2012 |
| EP | 2778913 | 9/2014 |
| EP | 2778914 | 9/2014 |
| EP | 2858018 | 4/2015 |
| EP | 2869211 | 5/2015 |
| EP | 2889814 | 7/2015 |
| EP | 2892197 | 7/2015 |
| EP | 2963595 | 1/2016 |
| EP | 2980748 | 2/2016 |
| GB | 2366498 | 3/2002 |
| GB | 2513472 | 10/2014 |
| GB | 2513721 | 11/2014 |
| GB | 2514239 | 11/2014 |
| GB | 2517582 | 2/2015 |
| NL | 2013134 | 1/2015 |
| WO | WO 01/025906 | 4/2001 |
| WO | WO 2001/088750 | 11/2001 |
| WO | WO 2005/116851 | 12/2005 |
| WO | WO 2008/113059 | 9/2008 |
| WO | WO 2009/051987 | 4/2009 |
| WO | WO 2009/061501 | 5/2009 |
| WO | WO 2010/030913 | 3/2010 |
| WO | WO 2010/030914 | 3/2010 |
| WO | WO 2010/030919 | 3/2010 |
| WO | WO 2012/119008 | 9/2012 |

OTHER PUBLICATIONS

Anonymous, "A Real-World Problem of Matching Records," Nov. 2006, <http://grupoweb.upf.es/bd-web/slides/ullman.pdf> pp. 1-16.

Brandel, Mary, "Data Loss Prevention Dos and Don'ts," <http://web.archive.org/web/20080724024847/http://www.csoonline.com/article/221272/Dos_and_Don_ts_for_Data_Loss_Prevention>, Oct. 10, 2007, pp. 5.

Notice of Allowance for U.S. Appl. No. 14/222,364 dated Jul. 27, 2017.

Official Communication for U.S. Appl. No. 14/222,364 dated Jun. 24, 2016.

Official Communication for U.S. Appl. No. 14/222,364 dated Dec. 9, 2015.

Official Communication for U.S. Appl. No. 14/289,596 dated Aug. 5, 2015.

Official Communication for U.S. Appl. No. 14/518,757 dated Dec. 10, 2014.

(56) References Cited

OTHER PUBLICATIONS

Official Communication for U.S. Appl. No. 14/975,215 dated Jan. 4, 2018.
"A First Look: Predicting Market Demand for Food Retail using a Huff Analysis," TRF Policy Solutions, Jul. 2012, pp. 30.
"A Tour of Pinboard," <http://pinboard.in/tour> as printed May 15, 2014 in 6 pages.
Abbey, Kristen, "Review of Google Docs," May 1, 2007, pp. 2.
Acklen, Laura, "Absolute Beginner's Guide to Microsoft Word 2003," Dec. 24, 2003, pp. 15-18, 34-41, 308-316.
Adams et al., "Worklets: A Service-Oriented Implementation of Dynamic Flexibility in Workflows," R. Meersman, Z. Tari et al. (Eds.): OTM 2006, LNCS, 4275, pp. 291-308, 2006.
AMNET, "5 Great Tools for Visualizing Your Twitter Followers," posted Aug. 4, 2010, http://www.amnetblog.com/component/content/article/115-5-grate-tools-for-visualizing-your-twitter-followers.html.
Ananiev et al., "The New Modality API," http://web.archive.org/web/20061211011958/http://java.sun.com/developer/technicalArticles/J2SE/Desktop/javase6/modality/ Jan. 21, 2006, pp. 8.
APPACTS, "Smart Thinking for Super Apps," <http://www.appacts.com> Printed Jul. 18, 2013 in 4 pages.
Apsalar, "Data Powered Mobile Advertising," "Free Mobile App Analytics" and various analytics related screen shots <http://apsalar.com> Printed Jul. 18, 2013 in 8 pages.
Bluttman et al., "Excel Formulas and Functions for Dummies," 2005, Wiley Publishing, Inc., pp. 280, 284-286.
Bugzilla@Mozilla, "Bug 18726—[feature] Long-click means of invoking contextual menus not supported," http://bugzilla.mozilla.org/show_bug.cgi?id=18726 printed Jun. 13, 2013 in 11 pages.
Capptain—Pilot Your Apps, <http://www.capptain.com> Printed Jul. 18, 2013 in 6 pages.
Celik, Tantek, "CSS Basic User Interface Module Level 3 (CSS3 UI)," Section 8 Resizing and Overflow, Jan. 17, 2012, retrieved from internet http://www.w3.org/TR/2012/WD-css3-ui-20120117/#resizing-amp-overflow retrieved on May 18, 2015.
Chaudhuri et al., "An Overview of Business Intelligence Technology," Communications of the ACM, Aug. 2011, vol. 54, No. 8.
Chen et al., "Bringing Order to the Web: Automatically Categorizing Search Results," CHI 2000, Proceedings of the SIGCHI conference on Human Factors in Computing Systems, Apr. 1-6, 2000, The Hague, The Netherlands, pp. 145-152.
Cohn, et al., "Semi-supervised clustering with user feedback," Constrained Clustering: Advances in Algorithms, Theory, and Applications 4.1 (2003): 17-32.
Conner, Nancy, "Google Apps: The Missing Manual," May 1, 2008, pp. 15.
Countly Mobile Analytics, <http://count.ly/> Printed Jul. 18, 2013 in 9 pages.
Definition "Identity", downloaded Jan. 22, 2015, 1 page.
Definition "Overlay", downloaded Jan. 22, 2015, 1 page.
Delicious, <http://delicious.com/> as printed May 15, 2014 in 1 page.
DISTIMO—App Analytics, <http://www.distimo.com/app-analytics> Printed Jul. 18, 2013 in 5 pages.
Dramowicz, Ela, "Retail Trade Area Analysis Using the Huff Model," Directions Magazine, Jul. 2, 2005 in 10 pages, http://www.directionsmag.com/articles/retail-trade-area-analysis-using-the-huff-model/123411.
"E-MailRelay," <http://web.archive.org/web/20080821175021/http://emailrelay.sourceforge.net/> Aug. 21, 2008, pp. 2.
Flurry Analytics, <http://www.flurry.com/> Printed Jul. 18, 2013 in 14 pages.
Galliford, Miles, "SnagIt Versus Free Screen Capture Software: Critical Tools for Website Owners," <http://www.subhub.com/articles/free-screen-capture-software>, Mar. 27, 2008, pp. 11.
GIS-NET 3 Public _ Department of Regional Planning. Planning & Zoning Information for UNINCORPORATED LA County. Retrieved Oct. 2, 2013 from http://gis.planning.lacounty.gov/GIS-NET3_Public/Viewer.html.

Google Analytics Official Website—Web Analytics & Reporting, <http://www.google.com/analytics.index.html> Printed Jul. 18, 2013 in 22 pages.
Gorr et al., "Crime Hot Spot Forecasting: Modeling and Comparative Evaluation", Grant 98-IJ-CX-K005, May 6, 2002, 37 pages.
"GrabUp—What a Timesaver!" <http://atlchris.com/191/grabup/>, Aug. 11, 2008, pp. 3.
Griffith, Daniel A., "A Generalized Huff Model," Geographical Analysis, Apr. 1982, vol. 14, No. 2, pp. 135-144.
Gu et al., "Record Linkage: Current Practice and Future Directions," Jan. 15, 2004, pp. 32.
Hansen et al., "Analyzing Social Media Networks with NodeXL: Insights from a Connected World", Chapter 4, pp. 53-67 and Chapter 10, pp. 143-164, published Sep. 2010.
Hibbert et al., "Prediction of Shopping Behavior Using a Huff Model Within a GIS Framework," Healthy Eating in Context, Mar. 18, 2011, pp. 16.
Hua et al., "A Multi-attribute Data Structure with Parallel Bloom Filters for Network Services", HiPC 2006, LNCS 4297, pp. 277-288, 2006.
Huff et al., "Calibrating the Huff Model Using ArcGIS Business Analyst," ESRI, Sep. 2008, pp. 33.
Huff, David L., "Parameter Estimation in the Huff Model," ESRI, ArcUser, Oct.-Dec. 2003, pp. 34-36.
"HunchLab: Heat Map and Kernel Density Calculation for Crime Analysis," Azavea Journal, printed from www.azavea.com/blogs/newsletter/v4i4/kernel-density-capabilities-added-to-hunchlab/ on Sep. 9, 2014, 2 pages.
JetScreenshot.com, "Share Screenshots via Internet in Seconds," <http://web.archive.org/web/20130807164204/http://www.jetscreenshot.com/>, Aug. 7, 2013, pp. 1.
Johnson, Maggie "Introduction to YACC and Bison", Handout 13, Jul. 8, 2005, in 11 pages.
Johnson, Steve, "Access 2013 on demand," Access 2013 on Demand, May 9, 2013, Que Publishing.
Jul. 2015 Update Appendix 1: Examples published by the USPTO, 22 pages.
Keylines.com, "An Introduction to KeyLines and Network Visualization," Mar. 2014, <http://keylines.com/wp-content/uploads/2014/03/KeyLines-White-Paper.pdf> downloaded May 12, 2014 in 8 pages.
Keylines.com, "KeyLines Datasheet," Mar. 2014, <http://keylines.com/wp-content/uploads/2014/03/KeyLines-datasheet.pdf> downloaded May 12, 2014 in 2 pages.
Keylines.com, "Visualizing Threats: Improved Cyber Security Through Network Visualization," Apr. 2014, <http://keylines.com/wp-content/uploads/2014/04/Visualizing-Threats1.pdf> downloaded May 12, 2014 in 10 pages.
Kontagent Mobile Analytics, <http://www.kontagent.com/> Printed Jul. 18, 2013 in 9 pages.
Kwout, <http://web.archive.org/web/20080905132448/http://www.kwout.com/> Sep. 5, 2008, pp. 2.
Lim et al., "Resolving Attribute Incompatibility in Database Integration: An Evidential Reasoning Appoach," Department of Computer Science, University of Minnesota, 1994, <http://reference.kfupm.edu.sa/content/r/e/resolving_attribute_incompatibility_in_d_531691.pdf> pp. 1-10.
Litwin et al., "Multidatabase Interoperability," IEEE Computer, Dec. 1986, vol. 19, No. 12, http://www.lamsade.dauphine.fr/~litwin/mdb-interoperability.pdf, pp. 10-18.
Liu, Tianshun, "Combining GIS and the Huff Model to Analyze Suitable Locations for a New Asian Supermarket in the Minneapolis and St. Paul, Minnesota USA," Papers in Resource Analysis, 2012, vol. 14, pp. 8.
Localytics—Mobile App Marketing & Analytics <http://www.localytics.com/> Printed Jul. 18, 2013 in 12 pages.
Madden, Tom, "Chapter 16: The BLAST Sequence Analysis Tool," The NCBI Handbook, Oct. 2002, pp. 1-15.
Manno et al., "Introducing Collaboration in Single-user Applications through the Centralized Control Architecture," 2010, pp. 10.
Manske, "File Saving Dialogs," <http://www.mozilla.org/editor/ui_specs/FileSaveDialogs.html>, Jan. 20, 1999, pp. 7.

(56) References Cited

OTHER PUBLICATIONS

Map of San Jose, CA. Retrieved Oct. 2, 2013 from http://maps.yahoo.com.
Map of San Jose, CA. Retrieved Oct. 2, 2013 from http://maps.bing.com.
Map of San Jose, CA. Retrieved Oct. 2, 2013 from http://maps.google.com.
Microsoft—Developer Network, "Getting Started with VBA in Word 2010," Apr. 2010, <http://msdn.microsoft.com/en-us/library/ff604039%28v=office.14%29.aspx> as printed Apr. 4, 2014 in 17 pages.
Microsoft Office—Visio, "About connecting shapes," <http://office.microsoft.com/en-us/visio-help/about-connecting-shapes-HP085050369.aspx> printed Aug. 4, 2011 in 6 pages.
Microsoft Office—Visio, "Add and glue connectors with the Connector tool," <http://office.microsoft.com/en-us/visio-help/add-and-glue-connectors-with-the-connector-tool-HA010048532.aspx?CTT=1> printed Aug. 4, 2011 in 1 page.
Microsoft Windows, "Microsoft Windows Version 2002 Print Out 2," 2002, pp. 1-6.
Microsoft, "Registering an Application to a URI Scheme," <http://msdn.microsoft.com/en-us/library/aa767914.aspx>, printed Apr. 4, 2009 in 4 pages.
Microsoft, "Using the Clipboard," <http://msdn.microsoft.com/en-us/library/ms649016.aspx>, printed Jun. 8, 2009 in 20 pages.
Mixpanel—Mobile Analytics, <https://mixpanel.com/> Printed Jul. 18, 2013 in 13 pages.
Nadeau et al., "A Survey of Named Entity Recognition and Classification," Jan. 15, 2004, pp. 20.
Nin et al., "On the Use of Semantic Blocking Techniques for Data Cleansing and Integration," 11th International Database Engineering and Applications Symposium, 2007, pp. 9.
Nitro, "Trick: How to Capture a Screenshot As PDF, Annotate, Then Share It," <http://blog.nitropdf.com/2008/03/04/trick-how-to-capture-a-screenshot-as-pdf-annotate-it-then-share/>, Mar. 4, 2008, pp. 2.
Online Tech Tips, "Clip2Net—Share files, folders and screenshots easily," <http://www.online-tech-tips.com/free-software-downloads/share-files-folders-screenshots/>, Apr. 2, 2008, pp. 5.
Open Web Analytics (OWA), <http://www.openwebanalytics.com/> Printed Jul. 19, 2013 in 5 pages.
O'Reilly.com, http://oreilly.com/digitalmedia/2006/01/01/mac-os-x-screenshot-secrets.html published Jan. 1, 2006 in 10 pages.
Piwik—Free Web Analytics Software. <http://piwik.org/> Printed Jul. 19, 2013 in 18 pages.
PYTHAGORAS COMMUNICATIONS LTD., "Microsoft CRM Duplicate Detection," Sep. 13, 2011, https://www.youtube.com/watch?v=j-7Qis0D0Kc.
Qiang et al., "A Mutual-Information-Based Approach to Entity Reconciliation in Heterogeneous Databases," Proceedings of 2008 International Conference on Computer Science & Software Engineering, IEEE Computer Society, New York, NY, Dec. 12-14, 2008, pp. 666-669.
"Refresh CSS Ellipsis When Resizing Container—Stack Overflow," Jul. 31, 2013, retrieved from internet http://stackoverflow.com/questions/17964681/refresh-css-ellipsis-when-resizing-container, retrieved on May 18, 2015.
Schroder, Stan, "15 Ways to Create Website Screenshots," <http://mashable.com/2007/08/24/web-screenshots/>, Aug. 24, 2007, pp. 2.
Sekine et al., "Definition, Dictionaries and Tagger for Extended Named Entity Hierarchy," May 2004, pp. 1977-1980.
Sigrist, et al., "PROSITE, a Protein Domain Database for Functional Characterization and Annotation," Nucleic Acids Research, 2010, vol. 38, pp. D161-D166.
SnagIt, "SnagIt 8.1.0 Print Out 2," Software release date Jun. 15, 2006, pp. 1-3.
SnagIt, "SnagIt 8.1.0 Print Out," Software release date Jun. 15, 2006, pp. 6.
SnagIt, "SnagIt Online Help Guide," <http://download.techsmith.com/snagit/docs/onlinehelp/enu/snagit_help.pdf>, TechSmith Corp., Version 8.1, printed Feb. 7, 2007, pp. 284.
StatCounter—Free Invisible Web Tracker, Hit Counter and Web Stats, <http://statcounter.com/> Printed Jul. 19, 2013 in 17 pages.
TestFlight—Beta Testing on the Fly, <http://testflightapp.com/> Printed Jul. 18, 2013 in 3 pages.
Trak.io, <http://trak.io/> printed Jul. 18, 2013 in 3 pages.
UserMetrix, <http://usermetrix.com/android-analytics> printed Jul. 18, 2013 in 3 pages.
Valentini et al., "Ensembles of Learning Machines", M. Marinaro and R. Tagliaferri (Eds.): WIRN VIETRI 2002, LNCS 2486, pp. 3-20.
Vose et al., "Help File for ModelRisk Version 5," 2007, Vose Software, pp. 349-353. [Uploaded in 2 Parts].
Wang et al., "Research on a Clustering Data De-Duplication Mechanism Based on Bloom Filter," IEEE 2010, 5 pages.
Warren, Christina, "TUAW Faceoff: Screenshot apps on the firing line," <http://www.tuaw.com/2008/05/05/tuaw-faceoff-screenshot-apps-on-the-firing-line/>, May 5, 2008, pp. 11.
WIKIPEDIA, "Multimap," Jan. 1, 2013, https://en.wikipedia.org/w/index.php?title=Multimap&oldid=530800748.
Zhao et al., "Entity Matching Across Heterogeneous Data Sources: An Approach Based on Constrained Cascade Generalization," Data & Knowledge Engineering, vol. 66, No. 3, Sep. 2008, pp. 368-381.
International Search Report and Written Opinion in Application No. PCT/US2009/056703 dated Mar. 15, 2010.
Notice of Acceptance for Australian Patent Application No. 2013251186 dated Nov. 6, 2015.
Notice of Allowance for U.S. Appl. No. 12/556,307 dated Jan. 4, 2016.
Notice of Allowance for U.S. Appl. No. 14/225,084 dated May 4, 2015.
Notice of Allowance for U.S. Appl. No. 14/265,637 dated Feb. 13, 2015.
Notice of Allowance for U.S. Appl. No. 14/304,741 dated Apr. 7, 2015.
Notice of Allowance for U.S. Appl. No. 14/319,161 dated May 4, 2015.
Notice of Allowance for U.S. Appl. No. 14/323,935 dated Oct. 1, 2015.
Notice of Allowance for U.S. Appl. No. 14/479,863 dated Mar. 31, 2015.
Notice of Allowance for U.S. Appl. No. 14/552,336 dated Nov. 3, 2015.
Notice of Allowance for U.S. Appl. No. 14/746,671 dated Jan. 21, 2016.
Notice of Allowance for U.S. Appl. No. 14/805,313 dated Jun. 15, 2016.
Notice of Allowance for U.S. Appl. No. 14/923,364 dated May 6, 2016.
Official Communication for Australian Patent Application No. 2013251186 dated Mar. 12, 2015.
Official Communication for Australian Patent Application No. 2014201506 dated Feb. 27, 2015.
Official Communication for Australian Patent Application No. 2014201507 dated Feb. 27, 2015.
Official Communication for Australian Patent Application No. 2014203669 dated May 29, 2015.
Official Communication for Canadian Patent Application No. 2831660 dated Jun. 9, 2015.
Official Communication for European Patent Application No. 09813700.3 dated Apr. 3, 2014.
Official Communication for European Patent Application No. 12181585.6 dated Sep. 4, 2015.
Official Communication for European Patent Application No. 14158958.0 dated Apr. 16, 2015.
Official Communication for European Patent Application No. 14158958.0 dated Jun. 3, 2014.
Official Communication for European Patent Application No. 14158977.0 dated Jun. 10, 2014.
Official Communication for European Patent Application No. 14158977.0 dated Apr. 16, 2015.
Official Communication for European Patent Application No. 14187996.5 dated Feb. 12, 2015.

(56) References Cited

OTHER PUBLICATIONS

Official Communication for European Patent Application No. 14191540.5 dated May 27, 2015.
Official Communication for European Patent Application No. 14200246.8 dated May 29, 2015.
Official Communication for European Patent Application No. 14200298.9 dated May 13, 2015.
Official Communication for European Patent Application No. 15156004.2 dated Aug. 24, 2015.
Official Communication for European Patent Application No. 15179122.5 dated Sep. 11, 2015.
Official Communication for European Patent Application No. 15181419.1 dated Sep. 29, 2015.
Official Communication for European Patent Application No. 15184764.7 dated Dec. 14, 2015.
Official Communication for Great Britain Patent Application No. 1404486.1 dated May 21, 2015.
Official Communication for Great Britain Patent Application No. 1404486.1 dated Aug. 27, 2014.
Official Communication for Great Britain Patent Application No. 1404489.5 dated May 21, 2015.
Official Communication for Great Britain Patent Application No. 1404489.5 dated Aug. 27, 2014.
Official Communication for Great Britain Patent Application No. 1404499.4 dated Jun. 11, 2015.
Official Communication for Great Britain Patent Application No. 1404499.4 dated Aug. 20, 2014.
Official Communication for Great Britain Patent Application No. 1404573.6 dated Sep. 10, 2014.
Official Communication for Great Britain Patent Application No. 1411984.6 dated Dec. 22, 2014.
Official Communication for Netherlands Patent Application No. 2011729 dated Aug. 13, 2015.
Official Communication for Netherlands Patent Application No. 2012417 dated Sep. 18, 2015.
Official Communication for Netherlands Patent Application No. 2012421 dated Sep. 18, 2015.
Official Communication for Netherlands Patent Application No. 2012438 dated Sep. 21, 2015.
Official Communication for Netherlands Patent Application No. 2013134 dated Apr. 20, 2015.
Official Communication for New Zealand Patent Application No. 622389 dated Mar. 20, 2014.
Official Communication for New Zealand Patent Application No. 622404 dated Mar. 20, 2014.
Official Communication for New Zealand Patent Application No. 622439 dated Mar. 24, 2014.
Official Communication for New Zealand Patent Application No. 622439 dated Jun. 6, 2014.
Official Communication for New Zealand Patent Application No. 622473 dated Jun. 19, 2014.
Official Communication for New Zealand Patent Application No. 622473 dated Mar. 27, 2014.
Official Communication for New Zealand Patent Application No. 622513 dated Apr. 3, 2014.
Official Communication for New Zealand Patent Application No. 624557 dated May 14, 2014.
Official Communication for New Zealand Patent Application No. 628161 dated Aug. 25, 2014.
Official Communication for U.S. Appl. No. 12/556,307 dated Oct. 1, 2013.
Official Communication for U.S. Appl. No. 12/556,307 dated Feb. 13, 2012.
Official Communication for U.S. Appl. No. 12/556,307 dated Mar. 14, 2014.
Official Communication for U.S. Appl. No. 12/556,307 dated Sep. 2, 2011.
Official Communication for U.S. Appl. No. 12/556,307 dated Jun. 9, 2015.
Official Communication for U.S. Appl. No. 12/556,321 dated Jun. 6, 2012.
Official Communication for U.S. Appl. No. 12/556,321 dated Dec. 7, 2011.
Official Communication for U.S. Appl. No. 12/556,321 dated Jul. 7, 2015.
Official Communication for U.S. Appl. No. 13/669,274 dated Aug. 26, 2015.
Official Communication for U.S. Appl. No. 13/669,274 dated May 6, 2015.
Official Communication for U.S. Appl. No. 13/827,491 dated Dec. 1, 2014.
Official Communication for U.S. Appl. No. 13/827,491 dated Jun. 22, 2015.
Official Communication for U.S. Appl. No. 13/827,491 dated Mar. 30, 2016.
Official Communication for U.S. Appl. No. 13/827,491 dated Oct. 9, 2015.
Official Communication for U.S. Appl. No. 13/831,791 dated Feb. 11, 2016.
Official Communication for U.S. Appl. No. 13/831,791 dated Mar. 4, 2015.
Official Communication for U.S. Appl. No. 13/831,791 dated Aug. 6, 2015.
Official Communication for U.S. Appl. No. 13/835,688 dated Jun. 17, 2015.
Official Communication for U.S. Appl. No. 13/835,688 dated Sep. 30, 2015.
Official Communication for U.S. Appl. No. 13/835,688 dated Jun. 7, 2016.
Official Communication for U.S. Appl. No. 13/949,043 dated Jan. 15, 2016.
Official Communication for U.S. Appl. No. 13/949,043 dated Oct. 15, 2013.
Official Communication for U.S. Appl. No. 13/949,043 dated May 7, 2015.
Official Communication for U.S. Appl. No. 14/014,313 dated Jun. 18, 2015.
Official Communication for U.S. Appl. No. 14/141,252 dated Oct. 8, 2015.
Official Communication for U.S. Appl. No. 14/170,562 dated Jul. 17, 2015.
Official Communication for U.S. Appl. No. 14/170,562 dated Mar. 19, 2014.
Official Communication for U.S. Appl. No. 14/170,562 dated Oct. 2, 2015.
Official Communication for U.S. Appl. No. 14/170,562 dated Sep. 25, 2014.
Official Communication for U.S. Appl. No. 14/170,562 dated Mar. 3, 2016.
Official Communication for U.S. Appl. No. 14/225,006 dated Sep. 10, 2014.
Official Communication for U.S. Appl. No. 14/225,006 dated Sep. 2, 2015.
Official Communication for U.S. Appl. No. 14/225,006 dated Dec. 21, 2015.
Official Communication for U.S. Appl. No. 14/225,006 dated Feb. 27, 2015.
Official Communication for U.S. Appl. No. 14/225,084 dated Sep. 11, 2015.
Official Communication for U.S. Appl. No. 14/225,084 dated Sep. 2, 2014.
Official Communication for U.S. Appl. No. 14/225,084 dated Feb. 20, 2015.
Official Communication for U.S. Appl. No. 14/225,084 dated Jan. 4, 2016.
Official Communication for U.S. Appl. No. 14/225,160 dated Feb. 11, 2015.
Official Communication for U.S. Appl. No. 14/225,160 dated Aug. 12, 2015.
Official Communication for U.S. Appl. No. 14/225,160 dated May 20, 2015.

(56) References Cited

OTHER PUBLICATIONS

Official Communication for U.S. Appl. No. 14/225,160 dated Oct. 22, 2014.
Official Communication for U.S. Appl. No. 14/225,160 dated Jul. 29, 2014.
Official Communication for U.S. Appl. No. 14/265,637 dated Sep. 26, 2014.
Official Communication for U.S. Appl. No. 14/289,596 dated Jul. 18, 2014.
Official Communication for U.S. Appl. No. 14/289,596 dated Jan. 26, 2015.
Official Communication for U.S. Appl. No. 14/289,596 dated Apr. 30, 2015.
Official Communication for U.S. Appl. No. 14/289,596 dated May 9, 2016.
Official Communication for U.S. Appl. No. 14/289,599 dated Jul. 22, 2014.
Official Communication for U.S. Appl. No. 14/289,599 dated May 29, 2015.
Official Communication for U.S. Appl. No. 14/289,599 dated Sep. 4, 2015.
Official Communication for U.S. Appl. No. 14/304,741 dated Mar. 3, 2015.
Official Communication for U.S. Appl. No. 14/304,741 dated Aug. 6, 2014.
Official Communication for U.S. Appl. No. 14/306,138 dated Dec. 24, 2015.
Official Communication for U.S. Appl. No. 14/306,138 dated Dec. 3, 2015.
Official Communication for U.S. Appl. No. 14/306,147 dated Dec. 24, 2015.
Official Communication for U.S. Appl. No. 14/319,161 dated Jan. 23, 2015.
Official Communication for U.S. Appl. No. 14/449,083 dated Mar. 12, 2015.
Official Communication for U.S. Appl. No. 14/449,083 dated Oct. 2, 2014.
Official Communication for U.S. Appl. No. 14/449,083 dated Aug. 26, 2015.
Official Communication for U.S. Appl. No. 14/449,083 dated Apr. 8, 2016.
Official Communication for U.S. Appl. No. 14/451,221 dated Oct. 21, 2014.
Official Communication for U.S. Appl. No. 14/463,615 dated Sep. 10, 2015.
Official Communication for U.S. Appl. No. 14/463,615 dated Nov. 13, 2014.
Official Communication for U.S. Appl. No. 14/463,615 dated May 21, 2015.
Official Communication for U.S. Appl. No. 14/463,615 dated Jan. 28, 2015.
Official Communication for U.S. Appl. No. 14/463,615 dated Dec. 9, 2015.
Official Communication for U.S. Appl. No. 14/479,863 dated Dec. 26, 2014.
Official Communication for U.S. Appl. No. 14/483,527 dated Jun. 22, 2015.
Official Communication for U.S. Appl. No. 14/483,527 dated Jan. 28, 2015.
Official Communication for U.S. Appl. No. 14/483,527 dated Oct. 28, 2015.
Official Communication for U.S. Appl. No. 14/516,386 dated Feb. 24, 2016.
Official Communication for U.S. Appl. No. 14/518,757 dated Dec. 1, 2015.
Official Communication for U.S. Appl. No. 14/518,757 dated Apr. 2, 2015.
Official Communication for U.S. Appl. No. 14/518,757 dated Jul. 20, 2015.
Official Communication for U.S. Appl. No. 14/552,336 dated Jul. 20, 2015.
Official Communication for U.S. Appl. No. 14/562,524 dated Nov. 10, 2015.
Official Communication for U.S. Appl. No. 14/562,524 dated Sep. 14, 2015.
Official Communication for U.S. Appl. No. 14/571,098 dated Nov. 10, 2015.
Official Communication for U.S. Appl. No. 14/571,098 dated Mar. 11, 2015.
Official Communication for U.S. Appl. No. 14/571,098 dated Aug. 24, 2015.
Official Communication for U.S. Appl. No. 14/571,098 dated Aug. 5, 2015.
Official Communication for U.S. Appl. No. 14/631,633 dated Sep. 10, 2015.
Official Communication for U.S. Appl. No. 14/676,621 dated Oct. 29, 2015.
Official Communication for U.S. Appl. No. 14/676,621 dated Jul. 30, 2015.
Official Communication for U.S. Appl. No. 14/746,671 dated Nov. 12, 2015.
Official Communication for U.S. Appl. No. 14/800,447 dated Dec. 10, 2015.
Official Communication for U.S. Appl. No. 14/805,313 dated Dec. 30, 2015.
Official Communication for U.S. Appl. No. 14/813,749 dated Sep. 28, 2015.
Official Communication for U.S. Appl. No. 14/842,734 dated Nov. 19, 2015.
Official Communication for U.S. Appl. No. 14/923,374 dated Feb. 9, 2016.
Official Communication for U.S. Appl. No. 14/958,855 dated May 4, 2016.
Official Communication for U.S. Appl. No. 14/975,215 dated May 19, 2016.
Official Communication for U.S. Appl. No. 14/975,215 dated Jun. 21, 2017.
Official Communication for U.S. Appl. No. 14/975,215 dated Nov. 4, 2016.
Official Communication for U.S. Appl. No. 15/017,324 dated Apr. 22, 2016.
Official Communication for U.S. Appl. No. 15/181,712 dated Oct. 12, 2016.
Official Communication for U.S. Appl. No. 15/181,712 dated Jul. 5, 2017.

* cited by examiner

FIG. 2

CHECKLIST 300 / 210

TASKS
- 214 — Inbox — 215 — 1644
- 216 — Archived

PROVIDERS — 217 Sort ▼
- Provider 218A
- Provider 218B
- Provider 218C
- Provider 218D
- Provider 218E
- Provider 218F
- Provider 218G
- Provider 218H
- Provider 218I
- Provider 218J
- Provider 218K
- Provider 218L 220 — CLAIMS ADJUSTMENTS | 27    212 — GAPS IN CARE | 116 — 222    227 — Sort ▼    230 / 332

27 NEW CLAIMS TO ADJUST ASSOCIATED WITH PROVIDER #1

| ☐ Patient #200016382 | Claim #155385 (2013-09-22) is missing asthma or COPD diagnosis. Member has asthma or COPD prescriptions in 2013 but no related diagnosis. |
| ☐ Patient #200010065 | Claim #95423 (2013-10-16) is missing diabetes diagnosis. Member has diabetes prescriptions in 2013 but no related diagnosis. |
| ☐ Patient #200047720 | Claim #453087 (2013-12-16) is missing diabetes diagnosis. Member has diabetes prescriptions in 2013 but no related diagnosis. |
| ☐ Patient #200004994 | Claim #47223 (2013-08-15) is missing diabetes diagnosis. Member has diabetes prescriptions in 2013 but no related diagnosis. |
| ☐ Patient #200002060 | Claim #19426 (2013-11-08) is missing diabetes diagnosis. Member has diabetes prescriptions in 2013 but no related diagnosis. |
| ☐ Patient #200039938 | Claim #379115 (2013-09-22) is missing diabetes diagnosis. Member has diabetes prescriptions in 2013 but no related diagnosis. |
| ☐ Patient #200030296 | Claim #287571 (2013-09-22) is missing diabetes diagnosis. Member has diabetes prescriptions in 2013 but no related diagnosis. |
| ☐ Patient #200043828 | Claim #416233 (2013-10-16) is missing diabetes diagnosis. Member has diabetes prescriptions in 2013 but no related diagnosis. |
| ☐ Patient #200040614 | Claim #385517 (2013-09-30) is missing diabetes diagnosis. Member has diabetes prescriptions in 2013 but no related diagnosis. |
| ☐ Patient #200030643 | Claim #290913 (2013-08-18) is missing cancer diagnosis. Member has cancer prescriptions in 2013 but no related diagnosis. |
| ☐ Patient #200033141 | Claim #314579 (2013-02-04) is missing diabetes diagnosis. Member has diabetes prescriptions in 2013 but no related diagnosis. |
| 👉 Patient #200029575 | Claim #280571 (2013-11-08) is missing diabetes diagnosis. Member has diabetes prescriptions in 2013 but no related diagnosis. |

CHECKLIST 300

TASKS
- Inbox 1643
- Archived

PROVIDERS (Sort)
- Provider 218A
- Provider 218B
- Provider 218C
- Provider 218D
- Provider 218E
- Provider 218F
- Provider 218G
- Provider 218H
- Provider 218I
- Provider 218J
- Provider 218K
- Provider 218L

CLAIMS ADJUSTMENTS | 26    GAPS IN CARE | 116

27 NEW CLAIMS TO ADJUST ASSOCIATED WITH PROVIDER #1

| | | |
|---|---|---|
| ☐ | Patient #200016382 | Claim #155385 (2013-09-22) is missing asthma or COPD diagnosis. Member has asthma or COPD prescriptions in 2013 but no related diagnosis. |
| ☐ | Patient #200010065 | Claim #95423 (2013-10-16) is missing diabetes diagnosis. Member has diabetes prescriptions in 2013 but no related diagnosis. |
| ☐ | Patient #200047720 | Claim #453087 (2013-12-16) is missing diabetes diagnosis. Member has diabetes prescriptions in 2013 but no related diagnosis. |
| ☐ | Patient #200004994 | Claim #47223 (2013-08-15) is missing diabetes diagnosis. Member has diabetes prescriptions in 2013 but no related diagnosis. |
| ☐ | Patient #200002060 | Claim #19426 (2013-11-08) is missing diabetes diagnosis. Member has diabetes prescriptions in 2013 but no related diagnosis. |
| ☐ | Patient #200039938 | Claim #379115 (2013-09-22) is missing diabetes diagnosis. Member has diabetes prescriptions in 2013 but no related diagnosis. |
| ☐ | Patient #200030296 | Claim #287571 (2013-09-22) is missing diabetes diagnosis. Member has diabetes prescriptions in 2013 but no related diagnosis. |
| ☐ | Patient #200043828 | Claim #416233 (2013-10-16) is missing diabetes diagnosis. Member has diabetes prescriptions in 2013 but no related diagnosis. |
| ☐ | Patient #200040614 | Claim #385517 (2013-09-30) is missing diabetes diagnosis. Member has diabetes prescriptions in 2013 but no related diagnosis. |
| ☐ | Patient #200030643 | Claim #290913 (2013-08-18) is missing cancer diagnosis. Member has cancer prescriptions in 2013 but no related diagnosis. |
| ☐ | Patient #200033141 | Claim #314579 (2013-02-04) is missing diabetes diagnosis. Member has diabetes prescriptions in 2013 but no related diagnosis. |

Sort

CHECKLIST 210

TASKS 214
Inbox 215  1643
Archived 216

PROVIDERS
Provider 218A
Provider 218B
Provider 218C
Provider 218D
Provider 218E
Provider 218F
Provider 218G
Provider 218H
Provider 218I
Provider 218J
Provider 218K
Provider 218L 340  342  344
Sort ▼

CLAIMS ADJUSTMENTS 220 | 1
GAPS IN CARE 212 | 0  222

Sort ▼ 227

332

1 ARCHIVED CLAIM TO ADJUST ASSOCIATED WITH PROVIDER #1

☑ Patient #200029575  Claim #28057 1 (2013-11-08) is missing diabetes diagnosis. Member has diabetes prescriptions in 2013 but no related diagnosis.

300

CHECKLIST 400

TASKS 214
Inbox 215 1644
Archived 216

| CLAIMS ADJUSTMENTS 220 | 27 | GAPS IN CARE 212 | 116 222 |

101 NEW ITEMS 433
- ▲ Patient #200010065  Make appointment for diabetes.  ☎ 742-999-2304  460
- ▲ Patient #200047720  Make appointment for IHD.  ☎ 135-096-0017  430
- ▲ Patient #200031034   ☎ 725-290-7404  432
- ▲ Patient #200034596  Make appointment for COPD.  ☎ 187-832-2108

15 APPOINTMENTS SCHEDULED 462
- 3 Patient #200018380   ☎ 089-378-0037
- 2 Patient #200013998   ☎ 371-029-7860
- 2 Patient #200025421  Member is due for a colorectal cancer screen.  ☎ 743-935-7653
- 2 Patient #200016382  Make appointment for asthma or COPD.  ☎ 125-044-7858
- 2 Patient #200028239   ☎ 877-555-0248

PROVIDERS 217
Sort ▼

Provider #1
Provider #2
Provider #3
Provider #4
Provider #5
Provider #6
Provider #7
Provider #8
Provider #9
Provider #10
Provider #11
Provider #12

242 / 240 / 244

Sort ▼ 227

FIG. 4

CHECKLIST 210

TASKS 214
Inbox 215 1644
Archived 216

| CLAIMS ADJUSTMENTS 220 | | 27 | GAPS IN CARE 212 | | 116 222 | Sort 227 |

101 NEW ITEMS 460

- ▲ Patient #200010065  Make appointment for diabetes.  ☎ 742-999-2304
- ▲ Patient #200047720  Make appointment for IHD.  ☎ 135-096-0017
- 2 Patient #200031034  Make appointment for COPD.  ☎ 725-290-7404
- 👆 Patient #200034596  534  ☎ 187-832-2108

15 APPOINTMENTS SCHEDULED 462

- 3 Patient #200018380  ☎ 089-378-0037
- 2 Patient #200025421  Member is due for a colorectal cancer screen.  ☎ 371-029-7860
- ▲ Patient #200013998  ☎ 743-935-7653
- 2 Patient #200016382  Make appointment for asthma or COPD.  ☎ 125-044-7858
- 2 Patient #200028239  ☎ 877-555-0248

550

PROVIDERS  Sort 217

- Provider #1
- Provider #2
- Provider #3
- Provider #4
- Provider #5
- Provider #6
- Provider #7
- Provider #8
- Provider #9
- Provider #10
- Provider #11
- Provider #12

CHECKLIST — 500

TASKS — 210

- Inbox — 214 — 1644 (215)
- Archived — 216

PROVIDERS — Sort (217)

- Provider #1
- Provider #2
- Provider #3
- Provider #4
- Provider #5
- Provider #6
- Provider #7
- Provider #8
- Provider #9
- Provider #10
- Provider #11
- Provider #12

CLAIMS ADJUSTMENTS | 27 (220) — GAPS IN CARE | 116 (222) — Sort (227)

101 NEW ITEMS — 430, 460

| | Patient # | Description | Phone |
|---|---|---|---|
| 3 | Patient #200010065 | Make appointment for diabetes. | 742-999-2304 |
| 2 | Patient #200047720 | Make appointment for IHD. | 135-096-0017 |
| 2 | Patient #200031034 | appointment for COPD. [Mark As Scheduled / Mark As Complete] — 534 | 725-290-7404 |
| | | | 187-832-2108 |

15 APPOINTMENTS SCHEDULED — 462

| 3 | Patient #200018380 | Member is due for a colorectal cancer screen. | 089-378-0037 |
| 2 | Patient #200013998 | | 371-029-7860 |
| 2 | Patient #200025421 | Make appointment for asthma or COPD. | 743-935-7653 |
| | Patient #200016382 | | 125-044-7858 |
| 2 | Patient #200028239 | | 877-555-0248 |

(552)

CHECKLIST 500

TASKS 210

Inbox 215 — 1644

Archived 217

| | CLAIMS ADJUSTMENTS 220 | 27 | GAPS IN CARE 222 | 116 |

100 NEW ITEMS 430

| 3 | Patient #200010065 | Make appointment for diabetes. | ☎ 742-999-2304 |
| 2 | Patient #200047720 | Make appointment for IHD. | ☎ 135-096-0017 |
| 2 | Patient #200031034 | | ☎ 725-290-7404 |

16 APPOINTMENTS SCHEDULED 462

| 3 | Patient #200018380 | | ☎ 089-378-0037 |
| 2 | Patient #200025421 | Member is due for a colorectal cancer screen. | ☎ 371-029-7860 |
| 2 | Patient #200016382 | Make appointment for asthma or COPD. | ☎ 743-935-7653 |
| 2 | Patient #200028239 | | ☎ 125-044-7858 |
| 2 | Patient #200034596 | Make appointment for COPD. | ☎ 187-832-2108 |

PROVIDERS 216

Provider #1
Provider #2
Provider #3
Provider #4
Provider #5
Provider #6
Provider #7
Provider #8
Provider #9
Provider #10
Provider #11
Provider #12

FIG. 5D

CHECKLIST 210

TASKS
Inbox 215 1644
Archived 217 Sort ▼

PROVIDERS
- Provider #1
- Provider #2
- Provider #3
- Provider #4
- Provider #5
- Provider #6
- Provider #7
- Provider #8
- Provider #9
- Provider #10
- Provider #11
- Provider #12

---

CLAIMS ADJUSTMENTS 220 | 27 212 | GAPS IN CARE 222 | 116  Sort ▼ 227

100 NEW ITEMS
- ▲ Patient #200010065 — Make appointment for diabetes. ☏ 742-999-2304
- ▲ Patient #200047720 — Make appointment for IHD. ☏ 135-096-0017
- 2 Patient #200031034 — ☏ 725-290-7404

16 APPOINTMENTS SCHEDULED
- 3 Patient #200018380 — ☏ 089-378-0037
- 2 Patient #200013998 — ☏ 371-029-7860
- ▲ Patient #200025421 — Member is due for a colorectal cancer screen. ☏ 743-935-7653
- ▲ Patient #200016382 — Make appointment for asthma or COPD. ☏ 125-044-7858
- 2 Patient #200028239 — ☏ 877-555-0248
- ▲ Patient #200034596 — Make appointment for COPD. ☏ 187-832-2108

FIG. 5E

CHECKLIST 500

TASKS 210
- Inbox 214 — 1643 215
- Archived 216

PROVIDERS 217
Provider #1 through Provider #12 (with bar charts 340, 342, 344)

CLAIMS ADJUSTMENTS 220 | 27 | GAPS IN CARE 212 | 115 222

100 NEW ITEMS 460
- [3] Patient #200010065 — Make appointment for diabetes. — 742-999-2304 430
- [2] Patient #200047720 — Make appointment for IHD. — 135-096-0017
- [2] Patient #200031034 — — 725-290-7404

15 APPOINTMENTS SCHEDULED 462
- [3] Patient #200018380 — — 089-378-0037
- [2] Patient #200013998 — — 371-029-7860
- [2] Patient #200025421 — Member is due for a colorectal cancer screen. — 743-935-7653
- [2] Patient #200016382 — Make appointment for asthma or COPD. — 125-044-7858
- [2] Patient #200028239 — — 877-555-0248

Sort 227

FIG. 5H

CHECKLIST 210

TASKS 214
- Inbox 215 — 1644
- Archived 216

PROVIDERS 217 (Sort)

Provider #1 through Provider #12 (bar charts) 242 / 240 / 244

CLAIMS ADJUSTMENTS 220 | 27    GAPS IN CARE 212 | 116    222    227 (Sort)

101 NEW ITEMS    460    430    432

| | | | |
|---|---|---|---|
| Patient #200010065 | Make appointment for diabetes. | | 742-999-2304 |
| Patient #200047720 | Make appointment for IHD. | | 135-096-0017 |
| Patient #200031034 | Make appointment for COPD. | | 725-290-7404 |
| Patient #200034596 | | | 187-832-2108 |

15 APPOINTMENTS SCHEDULED    462

| | | | |
|---|---|---|---|
| Patient #200018380 | | | 089-378-0037 |
| Patient #200013998 | | | 371-029-7860 |
| Patient #200025421 | Member is due for a colorectal cancer screen. | | 743-935-7653 |
| Patient #200016382 | Make appointment for asthma or COPD. | | 125-044-7858 |
| Patient #200028239 | | | 877-555-0248 |

CHECKLIST 210

TASKS
- Inbox 215 — 1644
- Archived 217

PROVIDERS
- Provider #1
- Provider #2
- Provider #3
- Provider #4
- Provider #5
- Provider #6
- Provider #7
- Provider #8
- Provider #9
- Provider #10
- Provider #11
- Provider #12

Sort ▼

| CLAIMS ADJUSTMENTS 220 | 27 | GAPS IN CARE 212 | 116 222 | Sort ▼ 227 |

101 NEW ITEMS 460

| | Patient | Task | Phone |
|---|---|---|---|
| ▲ | Patient #200010065 | Make appointment for diabetes. | 742-999-2304 |
| 2 | Patient #200047720 | Make appointment for IHD. | 135-096-0017 |
| 2 | Patient #200031034 | Member is due for a breast cancer screen. | 725-290-7404 |
| 2 | Patient #200031034 | Member is due for a colorectal cancer screen. | |
| ▲ | Patient #200034596 | Make appointment for COPD. | 187-832-2108 |

15 APPOINTMENTS SCHEDULED 462

| 3 | Patient #200018380 | Member is due for a colorectal cancer screen. | 089-378-0037 |
| 2 | Patient #200013998 | | 371-029-7860 |
| ▲ | Patient #200025421 | Make appointment for asthma or COPD. | 743-935-7653 |
| ▲ | Patient #200016382 | | 125-044-7858 |
| 2 | Patient #200028239 | | 877-555-0248 |

CHECKLIST 700

TASKS
- Inbox 1644
- Archived

PROVIDERS (Sort)
- Provider #1
- Provider #2
- Provider #3
- Provider #4
- Provider #5
- Provider #6
- Provider #7
- Provider #8
- Provider #9
- Provider #10
- Provider #11
- Provider #12

CLAIMS ADJUSTMENTS | 27 | GAPS IN CARE | 116 (Sort)

101 NEW ITEMS

| | Patient # | Task | Phone |
|---|---|---|---|
| ▲ | Patient #200010065 | Make appointment for diabetes. | 742-999-2304 |
| 2 | Patient #200047720 | Make appointment for IHD. | 135-096-0017 |
| 2 | Patient #200031034 | Member is due for a breast cancer screen. | 725-290-7404 |
| 2 | Patient #200031034 | Member is due for a colorectal cancer screen. SCHEDULED | |
| ▲ | Patient #200034596 | Make appointment for COPD. | 187-832-2108 |

15 APPOINTMENTS SCHEDULED

| | Patient # | Task | Phone |
|---|---|---|---|
| 3 | Patient #200018380 | Member is due for a colorectal cancer screen. | 089-378-0037 |
| 2 | Patient #200013998 | | 371-029-7860 |
| 2 | Patient #200031034 | Member is due for a colorectal cancer screen. | 725-290-7404 |
| ▲ | Patient #200016382 | Make appointment for asthma or COPD. | 125-044-7858 |
| 2 | Patient #200028239 | | 877-555-0248 |

FIG. 7B

PROVIDER PORTAL

CROSS-REFERENCE TO RELATED APPLICATIONS

This application is a continuation of U.S. patent application Ser. No. 14/222,364, entitled "PROVIDER PORTAL" and filed on Mar. 21, 2014, which is hereby incorporated by reference in its entirety.

TECHNICAL FIELD

The present disclosure relates to systems and techniques for data integration, analysis, and visualization.

BACKGROUND

Prior to the passing of the Patient Protection and Affordable Care Act (PPACA), insurers were permitted to charge higher premiums for individuals with preexisting conditions (e.g., cancer, heart disease, diabetes, etc.) because such individuals cost the insurer proportionally more in comparison to healthier members. This caused insurance for the sickest and oldest of Americans to be all but unaffordable in many cases. To combat this, individual plans offered via state and federally-administered exchanges are now limited in the scope of conditions that can be used in the pricing of a policy. For example, premiums can be adjusted upwards for individuals who are smokers and/or based on age. However, insurers cannot price the terminal cancer patient out of a policy. The most expensive premium for a given individual on a plan is also capped at three times the cheapest premium on the plan.

However, the fact remains that individuals with preexisting conditions still cost insurers more than healthy individuals. The government, worried that insurers may try to find ways to discriminate against the sickest individuals, implemented a program of risk adjustment. The premise is that insurers that can prove they are insuring a sicker population in comparison to other insurers will be eligible for transfer payments. Thus, insurers with healthier individuals will send money to those with sicker individuals.

In addition, every Medicare Advantage plan offered by insurers is given a rating according to a five-star quality rating system. The whole-number star rating is assigned by virtue of performance across over 50 individual metrics that come from the Healthcare Effectiveness Data and Information Set (HEDIS), the Consumer Assessment of Healthcare Providers and Systems (CAHPS), the Centers for Medicare and Medicaid Services (CMS), the Health Outcomes Survey (HOS), and/or the Independent Review Entity (IRE). The star rating may generally measure the quality of a plan and customer satisfaction with a plan.

Before the PPACA was implemented, insurers received bonus payments based upon the star ratings given to their plans. For example, insurers received a 5% bonus for 5 stars, a 4% bonus for 4 stars, and so forth. Under the PPACA, new performance payments have been added. For example, 4 or 5-star plans will get an additional 1.5% on top of the initial determined amount. These bonus payments increase over time, reaching towards 5% by 2014. Thus, the star rating system has gained more importance under the PPACA.

Over time, insurers can receive claims from healthcare providers. The claims can be used to determine transfer payments and star ratings. However, such a collection may include a large number of claims and/or related data that may be stored in an electronic data store or memory. For example, such a collection of claims may include hundreds of thousands, millions, tens of millions, hundreds of millions, or even billions of claims and/or related data, and may consume significant storage and/or memory. Determination, selection, and analysis of relevant claims and/or related data within such a collection may be extremely difficult for an insurer. Furthermore, processing of such a large collection of claims and/or related data (e.g., as an employee of an insurer uses a computer to sift and/or search through huge numbers of claims and/or related data) may be extremely inefficient and consume significant processing and/or memory resources.

SUMMARY

The systems, methods, and devices described herein each have several aspects, no single one of which is solely responsible for its desirable attributes. Without limiting the scope of this disclosure, several non-limiting features will now be discussed briefly.

Embodiments of the present disclosure relate to the automatic selection of a subset of the received claims and/or related data and to the generation of graphical user interfaces that display the subset. The subset of claims and/or related data may include far fewer claims and/or related data (e.g., several orders of magnitude smaller) than the collection described above. In various embodiments, the graphical user interfaces allow health insurance company personnel to identify patient diagnoses that are not accounted for by the health insurance company. Furthermore, the graphical user interfaces allow health insurance company personnel to identify patients that have not submitted claims for documented ailments or conditions. Accordingly, in an embodiment, processing of the subset of claims and/or related data may be to optimize computing resources as compared to the collection described above. Thus, the health insurance company may be able to improve its chances of receiving transfer payments from other health insurance companies and/or receiving higher star ratings.

One aspect of the disclosure provides a computing system configured to process a large amount of dynamically updating data. The computing system comprises a network interface coupled to a data network for receiving and transmitting one or more packet flows. The computing system further comprises a computer processor. The computing system further comprises a computer readable storage medium storing program instructions configured for execution by the computer processor in order to cause the computing system to access medical data associated with a plurality of patients, wherein the medical data comprises an ailment identified as affecting the respective patient. The computer readable storage medium further stores program instructions configured for execution by the computer processor in order to access a plurality of medical claims, wherein each medical claim corresponds to at least one of the plurality of patients and is associated with one of a plurality of healthcare providers. The computer readable storage medium further stores program instructions configured for execution by the computer processor in order to determine a first set of medical claims in the plurality of medical claims that comprise claims for reimbursement for treatments of ailments not identified as affecting the respective patient. The computer readable storage medium further stores program instructions configured for execution by the computer processor in order to generate a user interface comprising a provider window depicting a selectable list of one or more of the plurality of healthcare providers, and a claim adjustment window. The user interface may be configured to receive a selection of a first healthcare provider in the list of healthcare providers and, in response to selection of the first healthcare provider, display, in the claim adjustment window, one or more medical claims in the first set of medical claims that are each associated with the first healthcare provider.

The computing system of the preceding paragraph can have any sub-combination of the following features: the user interface further comprises a gaps in care window; where the program instructions are further configured to cause the computing system to determine a first set of patients in the plurality of patients that have not submitted, during a first period of time, a claim for reimbursement for a treatment of an ailment identified as affecting the respective patient, where the user interface is further configured to display, in the gaps in care window for each user in the first set of patients that is associated with the first healthcare provider, a notification to contact the respective patient; the user interface is further configured to display, in the provider window, a plurality of histograms, and where each histogram is associated with a healthcare provider in the plurality of healthcare providers; each histogram is configured to indicate a number of medical claims in the first set of medical claims that are associated with the respective provider when the claim adjustment window is selected; each histogram is configured to indicate a number of patients in the first set of patients that are associated with the respective provider when the gaps in care window is selected; each histogram comprises information displayed using a logarithmic scale; where the program instructions are further configured to cause the computing system to receive a selection of a first notification to contact a first patient in the first set of patients, where the user interface is configured to display, in the gaps in care window, a schedule window that overlaps at least a portion of the first notification, where the schedule window comprises an option to indicate that an appointment has been scheduled with the first patient and an option to indicate that the appointment with the first patient has been completed; the gaps in care window comprises a new window and a scheduled appointment window, where the new window comprises the first notification, and where the user interface is further configured to display, in the scheduled appointment window and not the new window, the first notification in connection with a selection of the option to indicate that the appointment has been scheduled with the first patient; the gaps in care window comprises a first notification to contact a first patient in the first set of patients and a notification number associated with the first notification that indicates a number of reasons to contact the first patients; the user interface is further configured to display, in the gaps in care window, a second notification to contact the first patient and a third notification to contact the first patient in connection with a selection of the first notification; and the user interface comprises a sort button, and where the sort button, when selected, causes the claim adjustment window to display the one or more medical claims in the first set of medical claims in one of an alphabetical order, an order based on date, or an order based on importance of the respective medical claim.

Another aspect of the disclosure provides a computer-implemented method of processing a large amount of dynamically updating data. The computer-implemented method comprises, as implemented by one or more computer systems comprising computer hardware and memory, the one or more computer systems configured with specific executable instructions, accessing medical data associated with a plurality of users, wherein the medical data comprises an ailment identified as affecting the respective user. The computer-implemented method further comprises accessing a plurality of user claims, wherein each user claim corresponds to at least one of the plurality of users and is associated with one of a plurality of healthcare providers. The computer-implemented method further comprises determining, based on the accessed medical data, a first set of users claims in the plurality of user claims that comprise claims for reimbursement for treatments of ailments not identified as affecting the respective user. The computer-implemented method further comprises generating a user interface comprising a provider window depicting a selectable list of one or more of the plurality of healthcare providers, and a claim adjustment window. The computer-implemented method further comprises receiving a selection of a first healthcare provider in the list of healthcare providers. In response to selection of the first healthcare provider, the computer-implemented method further comprises updating the claim adjustment window of the user interface to include one or more user claims in the first set of user claims that are each associated with the first healthcare provider.

The computer-implemented method of the preceding paragraph can have any sub-combination of the following features: the user interface further comprises a gaps in care window; where the computer-implemented method further comprises determining a first set of users in the plurality of users that have not submitted, during a first period of time, a claim for reimbursement for a treatment of an ailment identified as affecting the respective user, and updating the gaps in care window, for each user in the first set of users that is associated with the first healthcare provider, to include a notification to contact the respective user; and where the computer-implemented method further comprises updating the provider window to include a plurality of histograms, wherein each histogram is associated with a healthcare provider in the plurality of healthcare providers.

Another aspect of the disclosure provides a non-transitory computer-readable medium comprising one or more program instructions recorded thereon, the instructions configured for execution by a computing system comprising one or more processors in order to cause the computing system to access medical data associated with a plurality of users, wherein the medical data comprises an ailment identified as affecting the respective user. The computer-readable medium further comprises one or more program instructions configured for execution in order to cause the computing system to access a plurality of user claims, wherein each user claim corresponds to at least one of the plurality of users and is associated with one of a plurality of healthcare providers. The computer-readable medium further comprises one or more program instructions configured for execution in order to cause the computing system to determine a first set of users claims in the plurality of user claims that comprise claims for reimbursement for treatments of ailments not identified as affecting the respective user. The computer-readable medium further comprises one or more program instructions configured for execution in order to cause the computing system to generate a user interface comprising a selectable list of one or more of the plurality of healthcare providers. The computer-readable medium further comprises one or more program instructions configured for execution in order to cause the computing system to receive a selection of a first healthcare provider in the list of healthcare providers. The computer-readable medium further comprises one or more program instructions configured for execution in order to cause the computing system to, in response to selection of the first healthcare provider, update the user interface to include one or more user claims in the first set of user claims that are each associated with the first healthcare provider.

The non-transitory computer-readable medium of the preceding paragraph can have any sub-combination of the following features: where the instructions are further configured to cause the computing system to determine a first set of users in the plurality of users that have not submitted, during a first period of time, a claim for reimbursement for a treatment of an ailment identified as affecting the respective user, and update the user interface, for each user in the first set of users that is associated with the first healthcare provider, to include a notification to contact the respective user; where the instructions are further configured to cause the computing system to update the user interface to include a plurality of histograms, and where each histogram is associated with a healthcare provider in the plurality of healthcare providers; and each histogram is configured to indicate a number of user claims in the first set of user claims that are associated with the respective provider.

BRIEF DESCRIPTION OF THE DRAWINGS

FIG. 2 illustrates a user interface displaying claims adjustments for review.

FIGS. 3A-C illustrate user interfaces displaying the selection and archiving of a pending claim adjustment.

FIG. 4 illustrates a user interface displaying gaps in care for review.

FIGS. 5A-5K illustrate user interfaces displaying the selection, scheduling, and completion of a gaps in care item.

FIGS. 6A-6B illustrate user interfaces displaying the expansion of gaps in care items that have been combined for a single patient.

FIGS. 7A-7B illustrate user interfaces displaying the expansion of scheduled and unscheduled gaps in care items that have been combined for a single patient.

DETAILED DESCRIPTION OF SPECIFIC EMBODIMENTS

Overview

As described above, the Patient Protection and Affordable Care Act (PPACA) allows for insurers that can prove they are insuring a sicker population in comparison to other insurers to be eligible for transfer payments. Thus, insurers may have an incentive to ensure that their risk pool looks as unappealing as possible. In other words, insurers may have an incentive to make sure everyone with expensive chronic diseases or other ailments that are indicative of an unhealthy individual are properly accounted for.

In addition, as described above, every Medicare Advantage plan offered by insurers is given a rating according to a five-star quality rating system that has gained more importance under the PPACA. Thus, insurers may be looking to improve their plan ratings in order to receive the extra benefits provided by the PPACA.

Accordingly, disclosed herein are various systems and methods that allow insurers to collect and analyze medical and/or pharmaceutical claims such that the ailments of insured individuals can be properly accounted for and/or the star ratings for plans can be improved or at least maintained. For example, the various systems described herein may determine, based on received claims, patient diagnoses that are not accounted for by a health insurance company and display such information in a user interface. Thus, health insurance company personnel may be able to visually identify such discrepancies and update the health insurance company records accordingly. As another example, the various systems described herein may identify patients that have not submitted claims for documented ailments or conditions. Such information may be displayed in a user interface as well. Thus, health insurance company personnel may be able to identify patients who may not be seeking treatment (or may have failed to report that treatments were acquired) and contact such patients to schedule appointments, thereby working to improve and/or maintain a plan's star rating.

Claim Collection and Analysis System Overview

Figure 1:
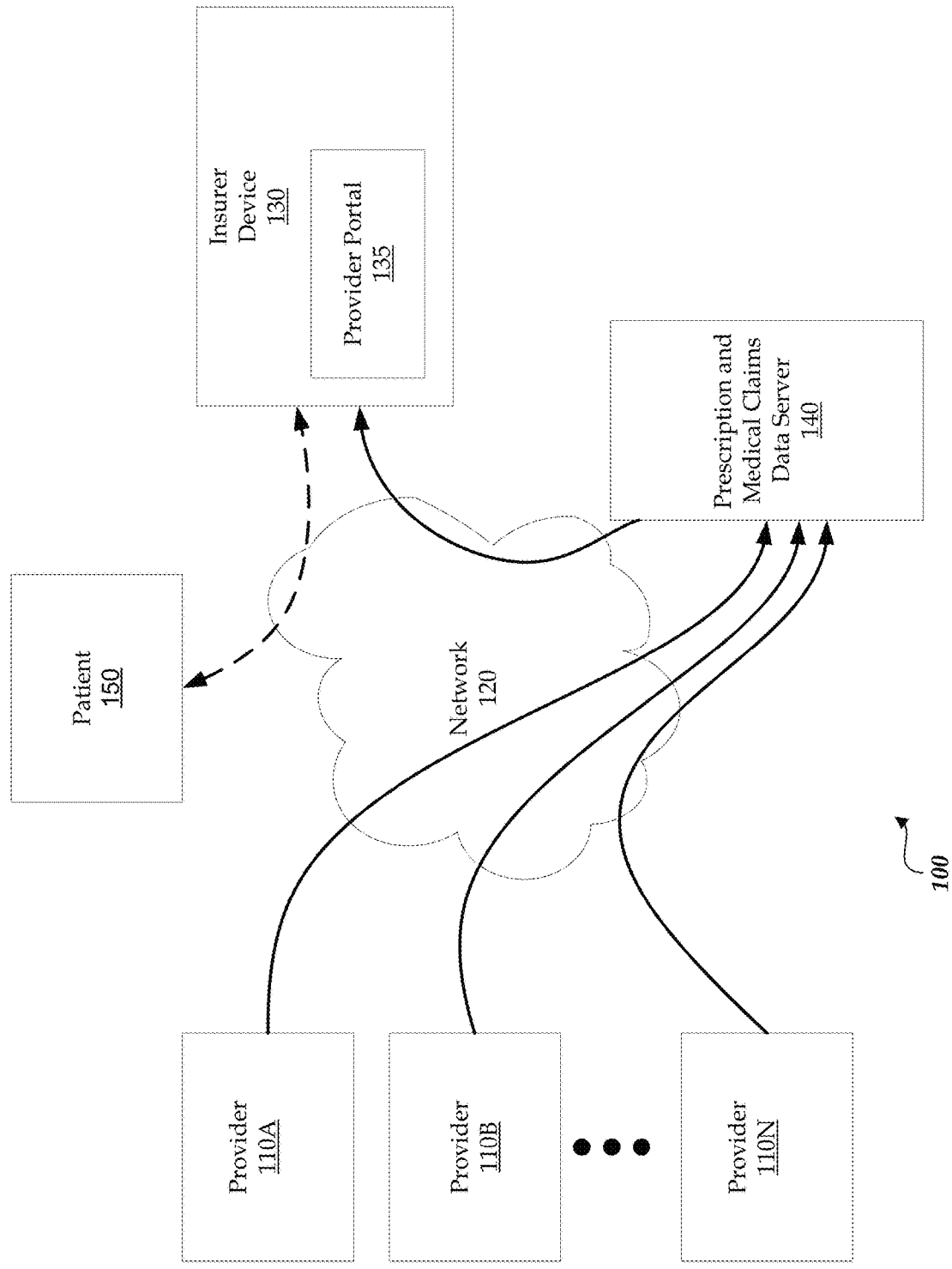
FIG. 1 illustrates a block diagram of a system for collecting and analyzing claims.

FIG. 1 illustrates a block diagram of a system 100 for collecting and analyzing claims. The system 100 comprises one or more providers 110, an insurer device 130, a provider portal 135, a prescription and medical claims data sever 140, a patient 150, and a network 120.

In the embodiment illustrated in FIG. 1, the one or more providers 110 (e.g., doctors, hospitals, pharmacies, etc.), which may be implemented by one or more first physical computing devices, are communicatively connected to the prescription and medical claims data server 140, which may be implemented by one or more second physical computing devices, over the network 120. Similarly, the insurer device 130 (e.g., operated by an insurance company, such as Blue Cross, Health Net, or Kaiser Permanente) may be implemented by one or more third physical computing devices and may be communicatively connected to the prescription and medical claims data server 140 over the network 120. The prescription and medical claims data server 140 can be operated by the insurance company or can be operated by a third party (e.g., a company that contracts with an insurance company, a healthcare provider, etc.). The patient 150, which may be implemented by one or more fourth physical computing devices, may likewise be communicatively connected to the insurer device 130 over the network 120. In some embodiments, each such physical computing device may be implemented as a computer system including some or all of the components illustrated in the example computing system 900 of FIG. 9. For example, the one or more providers 110, the insurer device 130, the prescription and medical claims data server 140, and/or the patient 150 may be implemented in a computer system as a set of program instructions recorded on a machine-readable storage medium.

The one or more providers 110 represent devices operated by healthcare providers (e.g., doctors, hospitals, pharmacies, etc.). Healthcare personnel (e.g., doctors, nurses, pharmacists, hospital or clinic staff, etc.) may submit medical and/or pharmaceutical claims to insurance companies (e.g., health insurance companies) on behalf of patients. Medical claims may include claims that are submitted to insurance companies to receive payment for medical services administered by the healthcare provider. Likewise, pharmaceutical claims may include claims that are submitted to insurance companies to receive payment for drugs distributed by the healthcare provider. These claims may be transmitted to the prescription and medical claims data server 140 for storage and/or for access by the insurer device 130. In some embodiments, information related to patient ailments entered into electronic medical record (EMR) systems (e.g., referred to herein as "EMR data") may also be transmitted to the prescription and medical claims data server 140 for storage and used in a manner as described herein with the medical and/or pharmaceutical claims. In some embodiments, lab claims and/or lab results may also be transmitted to the prescription and medical claims data server 140 for storage and used in a manner as described herein with the medical and/or pharmaceutical claims.

The insurer device 130 represents a device operated by a health insurance company that allows insurance company personnel to analyze pharmaceutical and/or medical claims received from the prescription and medical claims data server 140 and identify expected pharmaceutical and/or medical claims that were not received, for example. In an embodiment, the insurer device comprises a provider portal 135, which allows insurance company personnel to analyze claims, manipulate claims, identify claims that were not received, and/or contact patients via a graphical user interface (GUI). For example, the provider portal 135 may include GUI logic. The GUI logic may be a set of program instructions configured for execution by one or more computer processors of the insurer device 130, which are operable to receive user input and to display a graphical representation of claims using the approaches described herein. The GUI logic may be operable to receive user input from, and display a graphical representation of the claims, in a GUI that is provided on a display (not shown) of the insurer device 130 and/or another computing device that is in communication with the provider portal 135.

The prescription and medical claims data server 140 may be implemented as a special-purpose computer system having logical elements. In an embodiment, the logical elements may comprise program instructions recorded on one or more machine-readable storage media. Alternatively, the logical elements may be implemented in hardware, firmware, or a combination thereof.

When executed by one or more processors of the computer system, logic in the prescription and medical claims data server 140 is operable to receive, store, analyze, and/or manipulate claims and/or identify claims that were not received according to the techniques described herein. For example, the prescription and medical claims data server 140 may comprise the provider portal 135 (not shown), which can then be accessed by another device, such as the insurer device 130, via a network interface (e.g., a browser). In one embodiment, the provider portal 135 and/or the prescription and medical claims data server 140 may be implemented in a Java Virtual Machine (JVM) that is executing in a distributed or non-distributed computer system. In other embodiments, the provider portal 135 and/or the prescription and medical claims data server 140 may be implemented as a combination of programming instructions written in any programming language (e.g. C++ or Visual Basic) and hardware components (e.g., memory, CPU time) that have been allocated for executing the program instructions.

In an embodiment, the network 120 includes any communications network, such as the Internet. The network 120 may be a wired network, a wireless network, or a combination of the two. For example, network 120 may be a local area network (LAN) and/or a wireless area network (WAN).

Claims Adjustments

Figure 2:
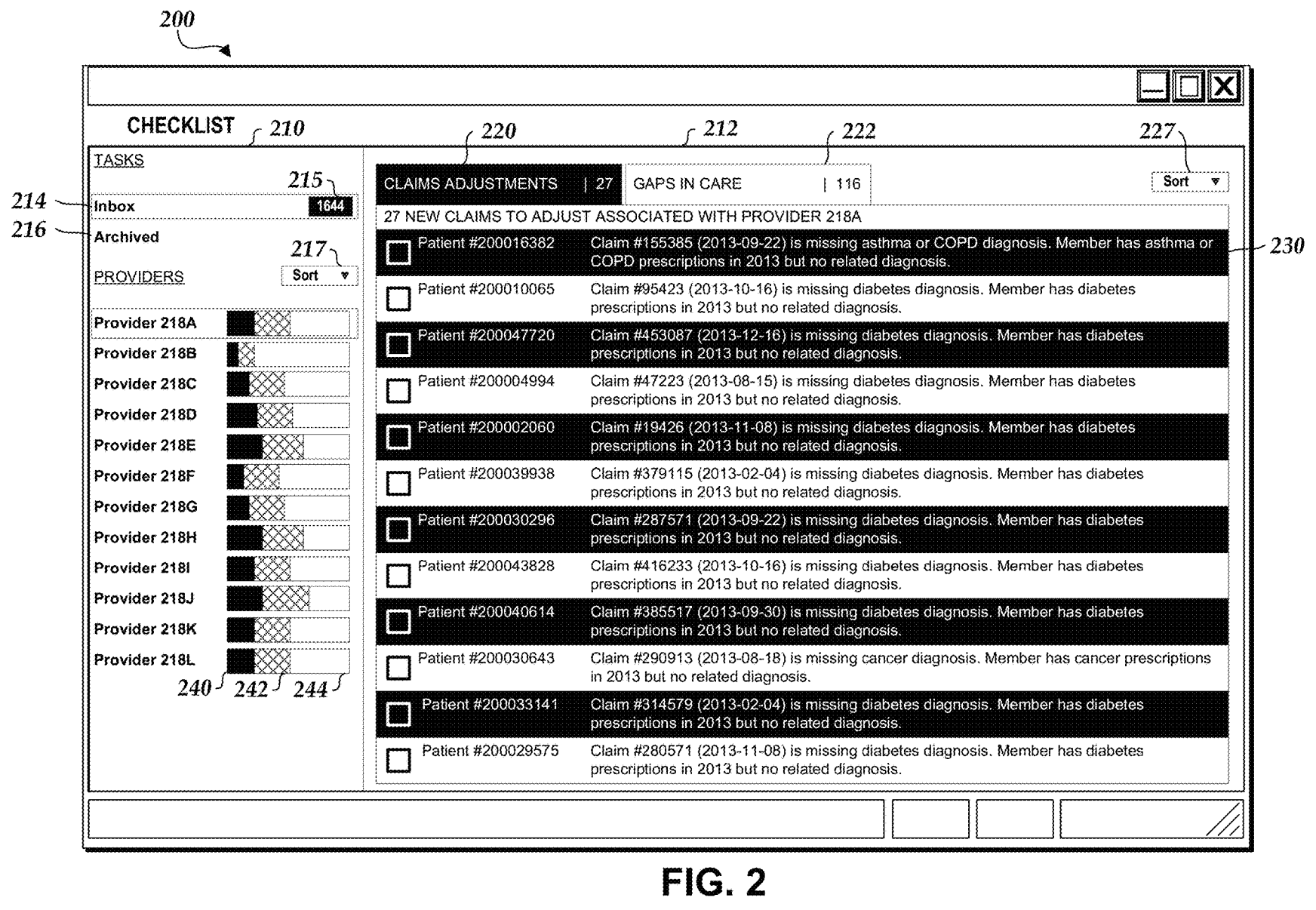

FIG. 2 illustrates a user interface 200 displaying claims adjustments for review. As illustrated in FIG. 2, the interface 200 includes a first pane 210 and a second pane 212. The first pane 210 may include a list of tasks and a list of healthcare providers. For example, the tasks may include an inbox 214 and an archived box 216. The list of healthcare providers may include healthcare providers 218A-L. For illustrative purposes, the inbox 214 and the healthcare provider 218A are selected in the first pane 210. The second pane 212 may include a claims adjustments tab 220 and a gaps in care tab 222. For illustrative purposes, the claims adjustments tab 220 is selected. The user interface 200 may be generated and/or displayed by the provider portal 135 as described above.

In an embodiment, the claim adjustments tab 220 includes a list of claims adjustments. As used herein, claims adjustments comprise claims for reimbursement submitted on behalf of individuals that relate to treatments for ailments or conditions not identified by an insurance company as affecting the respective individual. For example, the prescription and medical claims data server 140 may receive claims for reimbursements submitted on behalf of patients. The prescription and medical claims data server 140 and/or a data store accessible by the insurer device 130 (not shown) may store a record of the ailments or conditions a patient has been diagnosed with. Such record may be maintained by the health insurance company. The prescription and medical claims data server 140 and/or the insurer device 130 may compare patient diagnoses with claims submitted on behalf of the respective patients. Any claims that do not correspond with a patient diagnosis may be flagged and provided to the provider portal 135.

The claim adjustments tab 220 may include pending claims adjustments (e.g., claims adjustments for which corresponding patient records have not yet been updated) when the inbox 214 is selected. The claims adjustments tab 220 may include completed claims adjustments (e.g., claims adjustments for which corresponding patient records have been updated) when the archived box 216 is selected. For example, the insurer device 130 can be used to update the record of the ailments or conditions a patient has been diagnosed with based on the claims adjustments such that the records are kept accurate. Pending claims adjustments may indicate that the record has not been updated and completed claims adjustments may indicate that the record has been updated. Thus, the claim adjustments tab 220 allows health insurance company personnel to view unreported diagnoses and update their records accordingly to increase the possibility of receiving transfer payments from other health insurance companies and/or other third parties.

The claims adjustments that are displayed in the user interface 200 may be organized by healthcare providers. For example, the claim adjustments displayed when the claims adjustments tab 220 is selected and when the healthcare provider 218A is selected may be for individuals that are patients of the healthcare provider 218A. The claim adjustments tab 220 may indicate a number of claim adjustments that are associated with the selected healthcare provider 218A-L.

Each claim adjustment may include a patient identification and claim information. For example, claim adjustment 230 includes a patient identification of "Patient #200016382" and claim information including a claim number (e.g., Claim #155385), a date the claim was made (e.g., Sep. 22, 2013), and claim notes (e.g., a diagnosis that is missing, the type of prescriptions used by the individual, when the prescriptions were used, etc.).

The inbox 214 may be associated with task number 215. The task number 215 may represent a total number of pending claims adjustments and a total number of pending gaps in care, which are described in greater detail below, for all individuals associated with the healthcare providers 218A-L.

The first pane 210 may further include a sort button 217. When selected, a user may be able to sort healthcare providers 218A by name, by location, by type of practice, by number of claims adjustments, by number of gaps in care, by risk posed by the healthcare provider (e.g., a larger number of claims adjustments and/or gaps in care may be riskier than a smaller number of the same), and/or the like.

Likewise, the second pane 212 may include a sort button 227. When selected, a user may be able to sort the claim adjustments listed in the claim adjustments tab 220 by patient name or number, by date, by type of ailment or condition, by importance, severity, or urgency (e.g., a missed diagnosis of cancer may be considered more important to record than a missed diagnosis of depression), and/or the like.

In an embodiment, the first pane 210 includes graphs, such as histograms or stacked bar graphs, associated with each of the healthcare providers 218A-L. For example, the healthcare provider 218L is associated with the graph 244. Each graph includes a first box that represents a number of pending claims adjustments and a second box that represents a number of pending gaps in care. For example, the graph 244 includes first box 240 and second box 242. The graphs may be based on a linear scale, a logarithmic scale, and/or the like. Each of the graphs may have the same and/or a different scale. Thus, the width of the first box and/or the second box may represent an absolute number of claims adjustments or gaps in care when compared to the widths of other first boxes and second boxes and/or may represent a relative number of claims adjustments to gaps in care with respect to the particular healthcare provider.

FIGS. 3A-C illustrate user interfaces 300 displaying the selection and archiving of a pending claim adjustment 332. As illustrated in FIG. 3A, a user on behalf of a health insurance company, using a cursor 350, may select the claim adjustment 332. For example, the user may select the claim adjustment 332 by placing the cursor 350 over a portion of the claim adjustment 332 (e.g., the box in the claim adjustment 332 next to the patient identification) and performing a selection operation (e.g., clicking a mouse button, tapping a touch interface, double-tapping a touch interface, etc.). The claim adjustment 332 may be selected by the user if the user has cleared the claim (e.g., updated the insurance company records such that the diagnosed ailment or condition of the patient is recorded accordingly). As illustrated in FIG. 3A, the cursor 350 is a mouse pointer, but may be any other indicia in other embodiments.

As illustrated in FIG. 3B, once the claim adjustment 332 is selected, the claim adjustment 332 disappears from the claim adjustments 220 tab. In addition, the task number 215 is reduced (e.g., from 1644 to 1643) and the number of claims adjustments listed in the claims adjustments tab 220 is reduced. Furthermore, in a graph 344 associated with the healthcare provider 218A, the width of a first box 340 may be reduced to reflect the reduced number of pending claims adjustments. The claim adjustment 332 is moved to the archived box, which is displayed when the archived box 216 is selected, as illustrated in FIG. 3C.

FIG. 4 illustrates a user interface 400 displaying gaps in care for review. As illustrated in FIG. 4, the gaps in care tab 222 is selected. As used herein, gaps in care are items that indicate a patient or healthcare provider has not submitted a claim for reimbursement for a treatment of an ailment or condition identified as affecting the patient at some previous time. A gaps in care item may be generated if the claim has not been submitted within a certain period of time (e.g., a calendar year). For example, a patient may have been diagnosed with diabetes, yet the patient may not have scheduled an appointment to treat the condition during the calendar year. Thus, a gaps in care item may be generated for the patient. Generation of the gaps in care item may also depend on the eligibility of a patient (e.g., gender, age, etc.). As described above, the prescription and medical claims data server 140 and/or a data store accessible by the insurer device 130 (not shown) may store a record of the ailments or conditions a patient has been diagnosed with. Such data may be received directly from the providers 110. Such data may also be generated based on appointment information received and stored by the prescription and medical claims data server 140 and/or the data store accessible by the insurer device 130. The appointment information may include information relating to the last appointments scheduled (and attended) by the patient for a particular ailment or condition. The prescription and medical claims data server 140 and/or the insurer device 130 may compare patient diagnoses with claims submitted on behalf of the respective patients. If no claims correspond with a particular patient diagnosis, the lack of a claim for that patient may be flagged and provided to the provider portal 135.

In an embodiment, the gaps in care tab 222 includes a new items window 460 and a scheduled appointments window 462. The new items window 460 includes pending gaps in care items (e.g., gaps in care items for which appointments with patients have not been scheduled) and the scheduled appointments window 462 includes scheduled gaps in care items (e.g., gaps in care items for which appointments with patients have been scheduled).

A gaps in care item may include a patient identification, notes, and/or contact information for the patient. For example, the gaps in care item 430 includes a patient identification (e.g., Patient #200010065), notes (e.g., make appointment for diabetes), and a phone number for the patient. The contact information (e.g., the phone number) may be selected to connect the user with the patient, such as the patient 150 as illustrated in FIG. 1.

In some embodiments, there are multiple gaps in care items associated with a single patient. In such circumstances, the gaps in care items may be grouped together and such grouping may be indicated. For example, the gaps in care item 432 includes a box 433 with a number inside (e.g., 2). The number may represent a number of gaps in care items associated with the patient.

The graphs in the first pane 210 may transition from one view when the claims adjustments tab 220 is selected to a second view when the gaps in care tab 222 is selected. For example, the first box and the second box may switch places, visualized via a continuous animation. As illustrated in FIG. 4, the second box 242 and the first box 240 in the graph 244 have switched places.

Figure 5C:
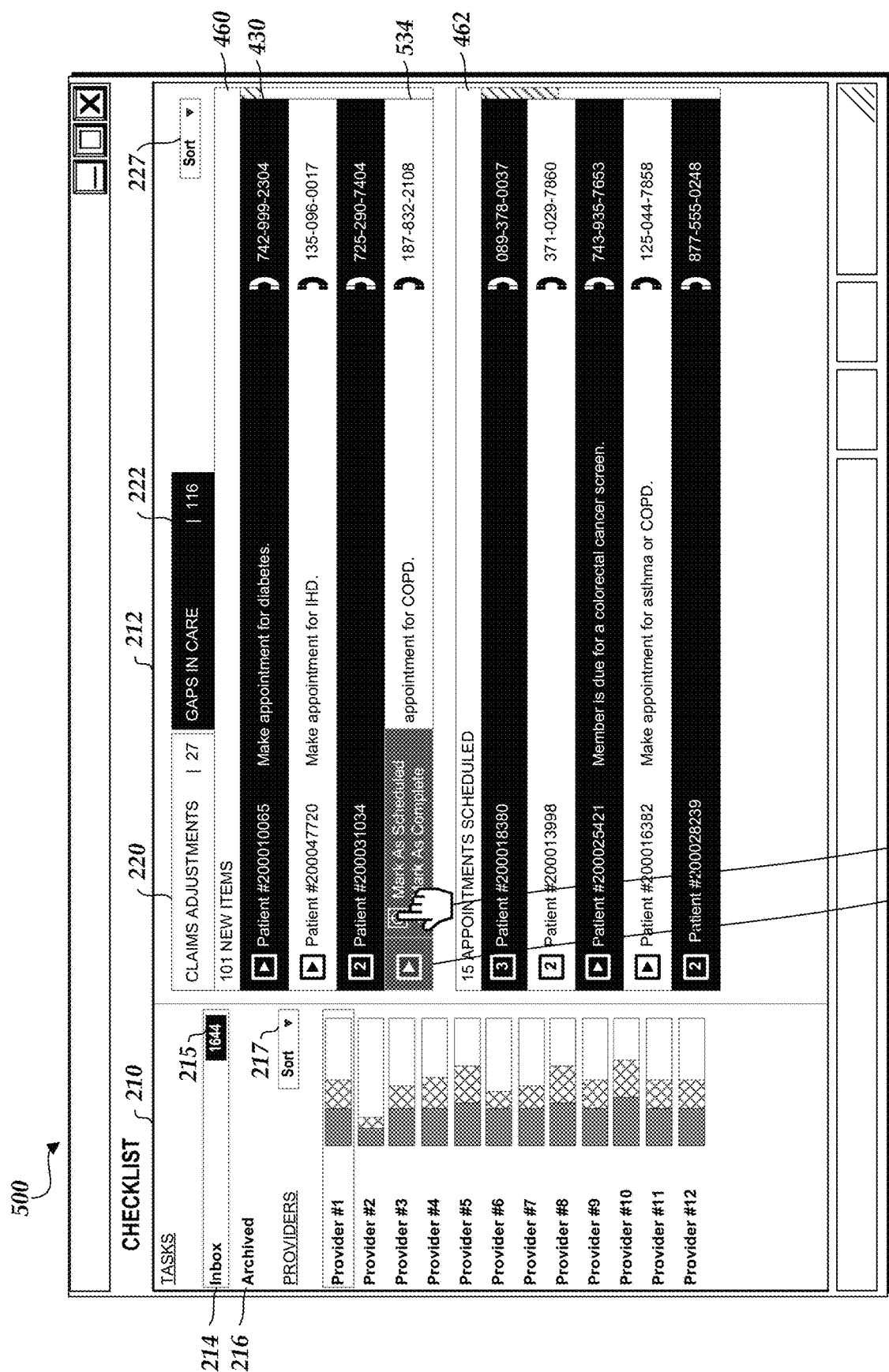

FIGS. 5A-5K illustrate user interfaces 500 displaying the selection, scheduling, and completion of a gaps in care item 534. As illustrated in FIG. 5A, a user on behalf of a health insurance company, using a cursor 550, may select the gaps in care item 534. When the sort button 227 is selected, a user may be able to sort the gaps in care items listed in the gaps in care tab 222 by patient name or number, by date, by type of ailment or condition, by importance, severity, or urgency (e.g., a missed appointment for cancer treatments may be considered more important to identify than a missed appointment for treatments for depression), and/or the like.

The gaps in care item 534 may be selected by the user if the user has contacted the patient to schedule an appointment and/or if the appointment has occurred, for example. As illustrated in FIG. 5B, a window 552 appears in the new items window 460 when a gaps in care item, such as the gaps in care item 534, is selected. The window 552 may comprise a "mark as scheduled" selection and a "mark as complete" selection. As illustrated in FIG. 5C, the user using the cursor 550 may select either selection. If "mark as scheduled" is selected, the gaps in care item 534 is moved from the new items window 460 to the scheduled appointments window 462, as illustrated in FIG. 5D. Alternatively, if "mark as complete" is selected, the gaps in care item 534 is removed from the new items window 460 and is visible when the archived box 216 is selected (e.g., which displays gaps in care items that are completed), as illustrated in FIG. 5I.

Figure 5F:
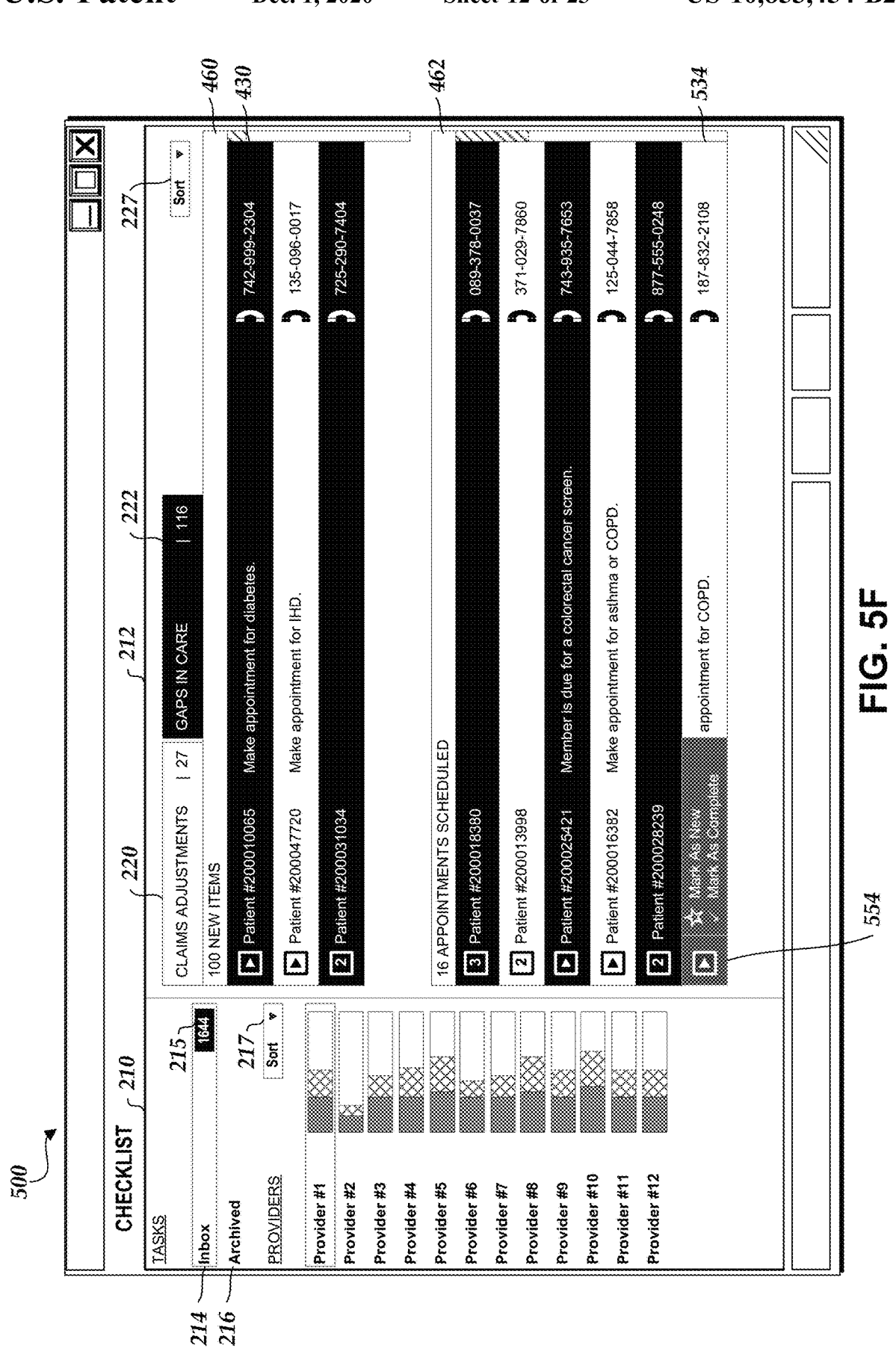
Figure 5G:
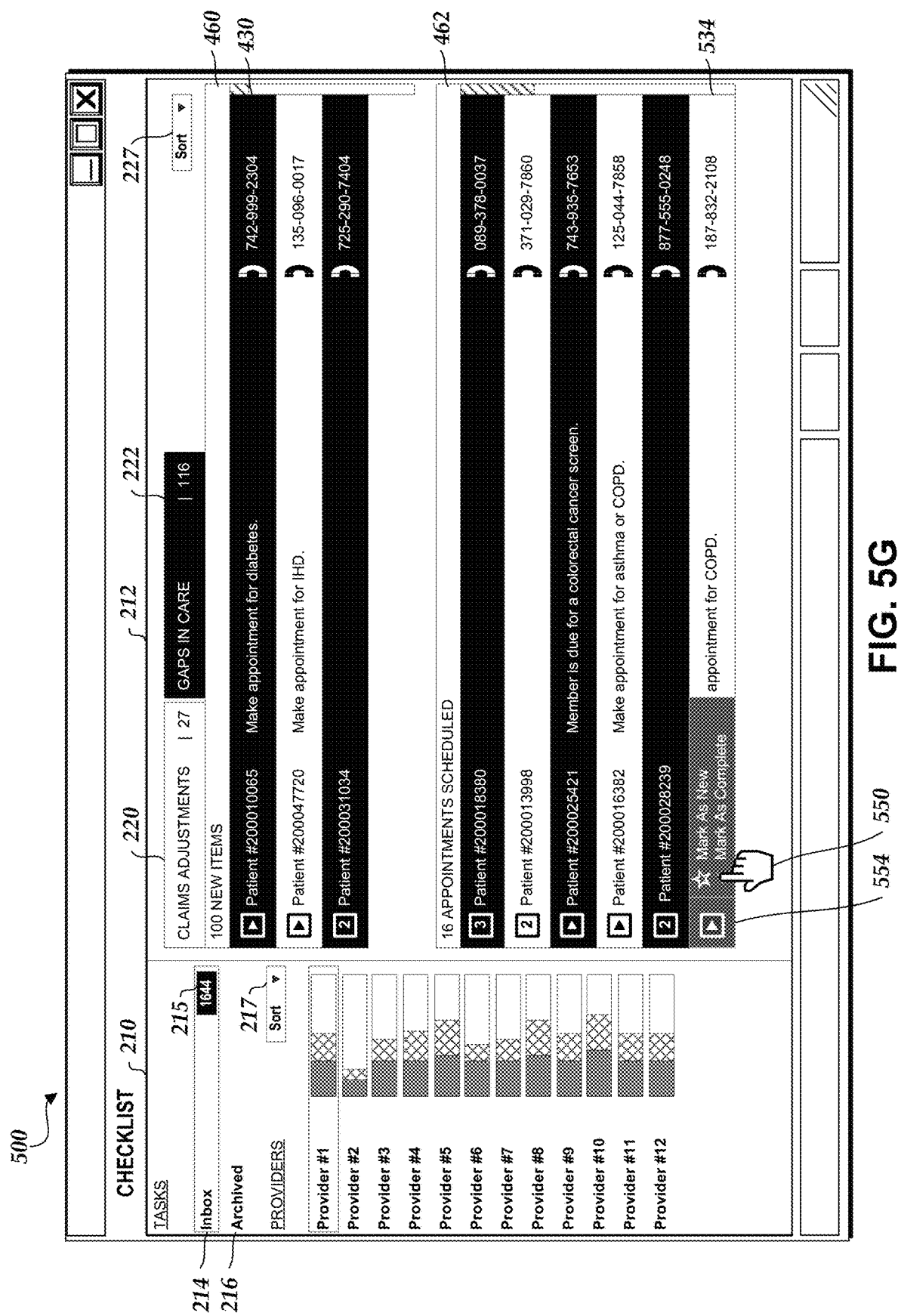

As illustrated in FIG. 5E, the user may select the gaps in care item 534 when it appears in the scheduled appointments window 462 using the cursor 550. Upon selecting a gaps in care item in the scheduled appointments window 462, such as the gaps in care item 534, a window 554 may appear in the scheduled appointments window 462, as illustrated in FIG. 5F. The window 554 may comprise a "mark as new" selection and a "mark as complete" selection. As illustrated in FIG. 5G, the user using the cursor 550 may select either selection. If "mark as new" is selected, the gaps in care item 534 is moved from the scheduled appointments window 462 to the new items window 460, as illustrated in FIG. 5A. Alternatively, if "mark as complete" is selected, the gaps in care item 534 is removed from the scheduled appointments window 462, as illustrated in FIG. 5H, and is visible when the archived box 216 is selected, as illustrated in FIG. 5I.

Furthermore, as illustrated in FIG. 5H, the task number 215 may decrease (e.g., from 1644 to 1643) once a gaps in care item, such as the gaps in care item 534, is marked as complete. In addition, the second box 342 may be adjusted (e.g., the width of the second box 342 may be reduced) to reflect the completion of a gaps in care item.

Figure 5I:
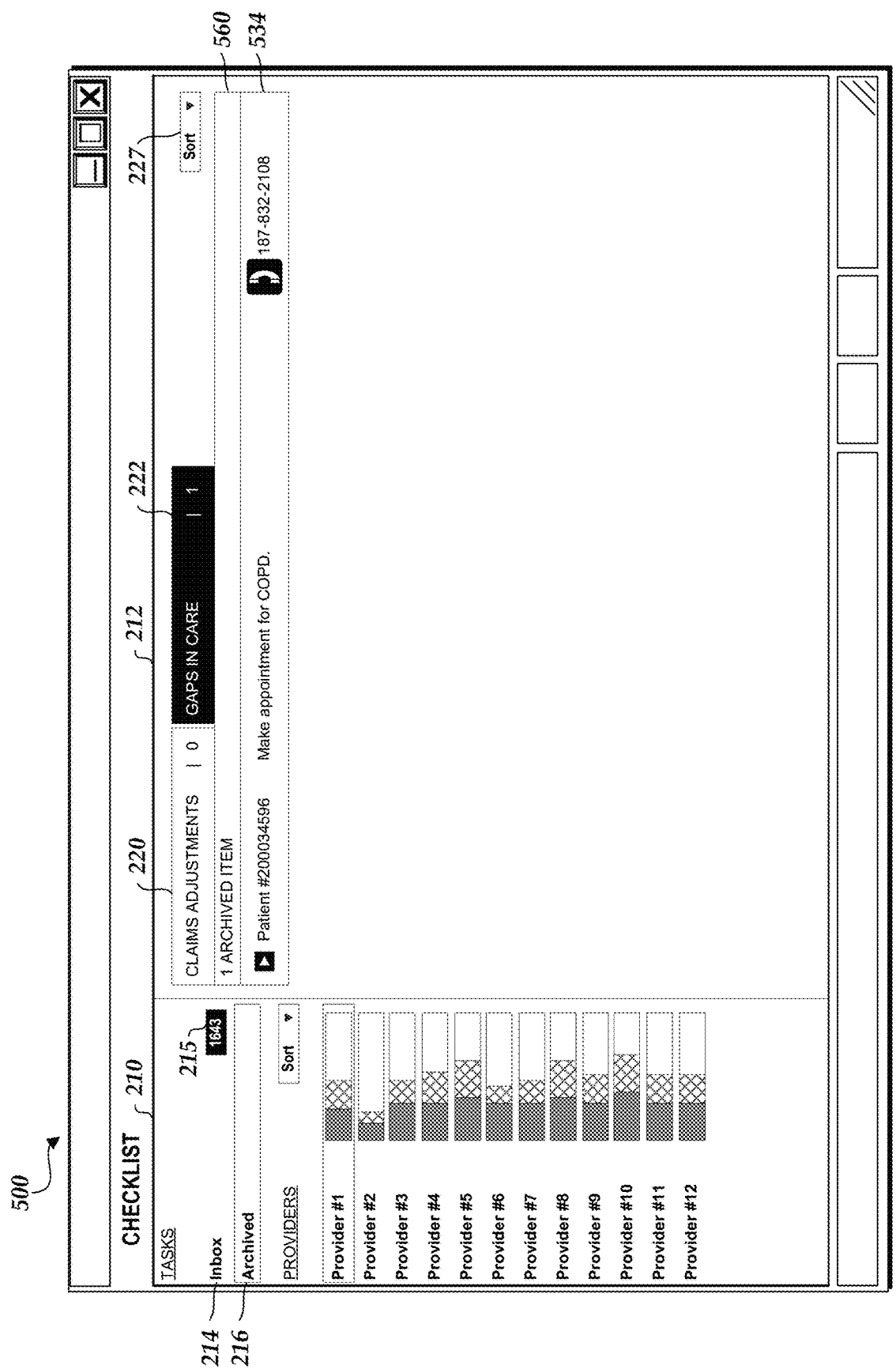
Figure 5J:
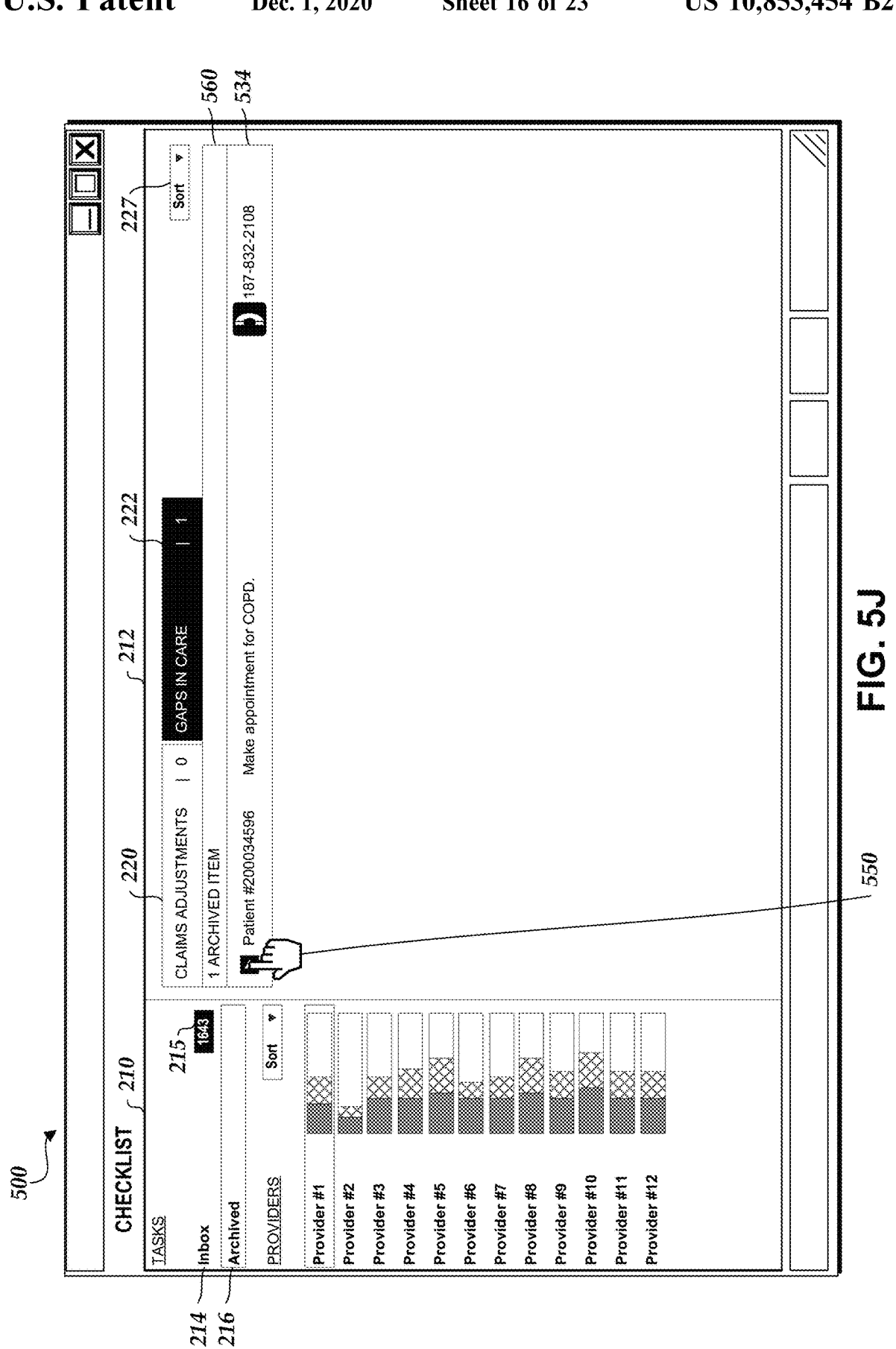

As illustrated in FIG. 5I, the user may select the archived box 216 to view completed gaps in care items. The completed gaps in care items may be displayed in an archived item window 560. As illustrated in FIG. 5J, the user may select the gaps in care item 534 using the cursor 550.

Figure 5K:
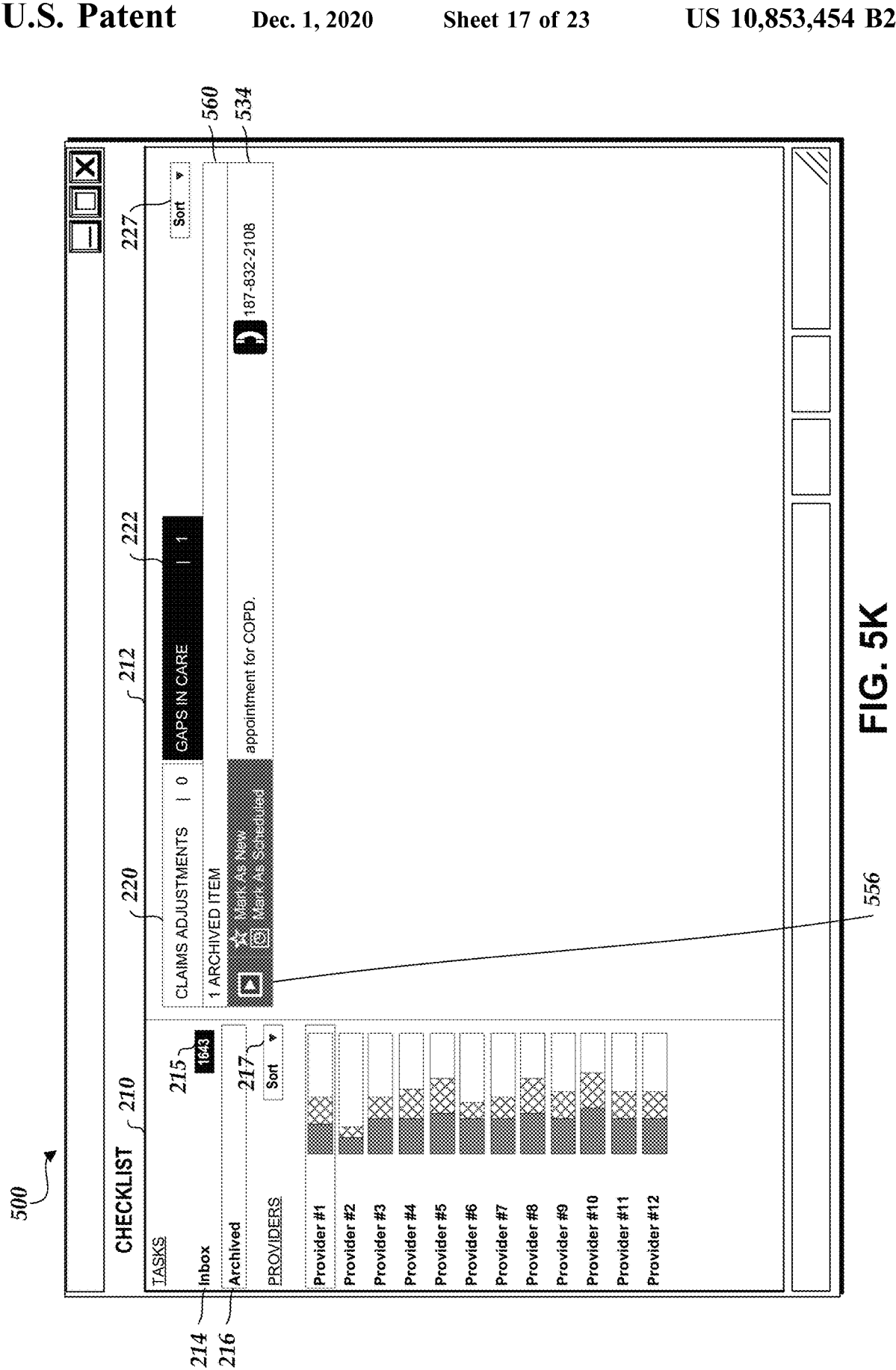

Upon selection of the gaps in care item 534, a window 556 may appear in the archived item window 560, as illustrated in FIG. 5K. The window 556 may comprise a "mark as new" selection and a "mark as scheduled" selection. If "mark as new" is selected, the gaps in care item 534 is moved from the archived item window 560 to the new items window 460, as illustrated in FIG. 5A. Alternatively, if "mark as scheduled" is selected, the gaps in care item 534 is moved from the archived item window 560 to the scheduled appointments window 462, as illustrated in FIG. 5D.

FIGS. 6A-6B illustrate user interfaces 600 displaying the expansion of gaps in care items that have been combined for a single patient. As illustrated in FIG. 6A, the user may select the gaps in care item 432, which is a gaps in care item that indicates multiple gaps in care items are associated with the patient, using a cursor 650. In an embodiment, upon selection of the gaps in care item 432, the gaps in care item 432 expands to show gaps in care items 632A-B, which are both associated with the same patient, as illustrated in FIG. 6B.

Figure 7A:
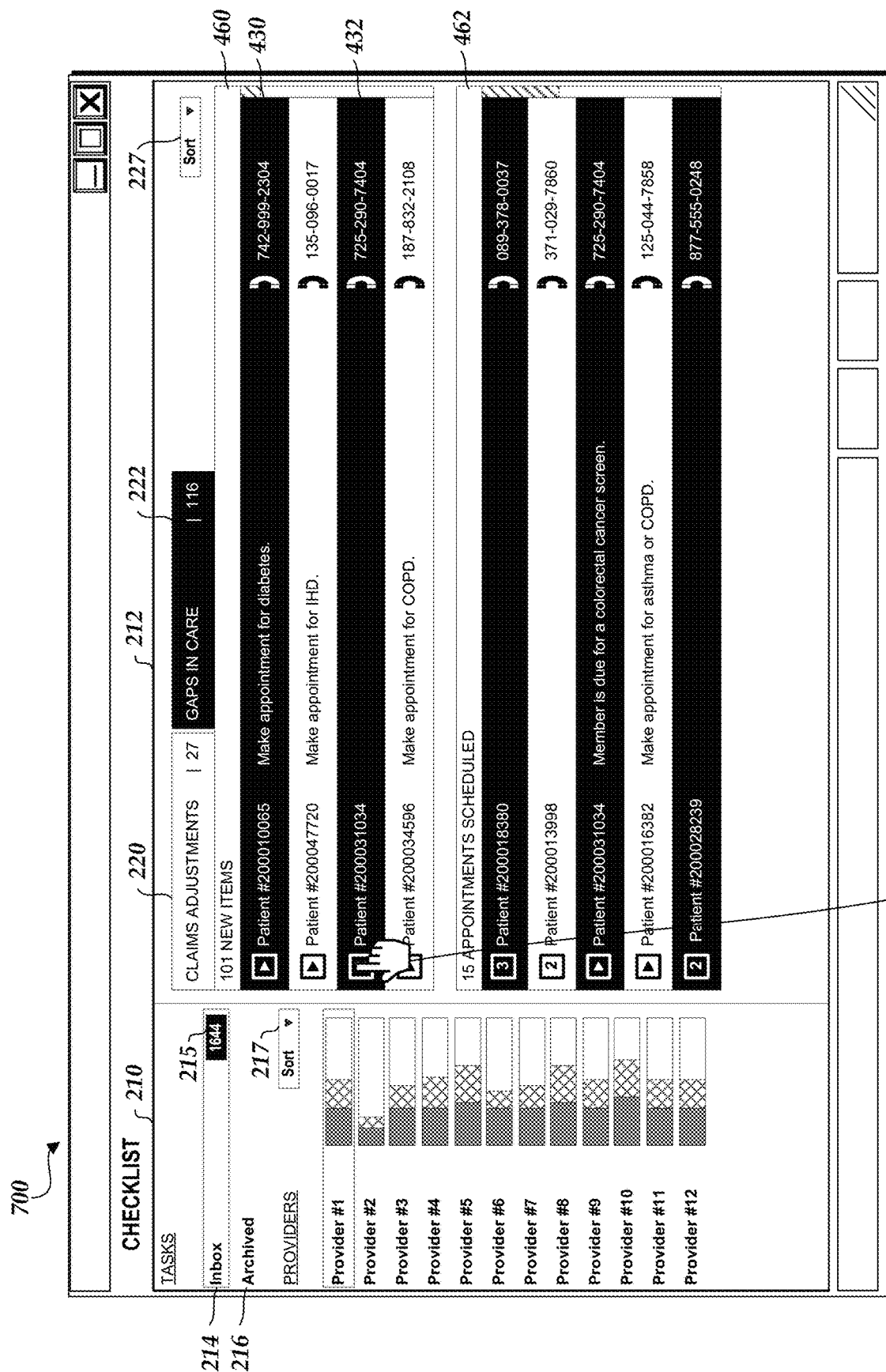

FIGS. 7A-7B illustrate user interfaces 700 displaying the expansion of scheduled and unscheduled gaps in care items that have been combined for a single patient. As illustrated in FIG. 7A, the user may select the gaps in care item 432 using a cursor 750. In an embodiment, upon selection of the gaps in care item 432, the gaps in care item 432 expands to show gaps in care items 732A-B, which are both associated with the same patient, as illustrated in FIG. 7B.

FIG. 7B further illustrates that the gaps in care item 732B has already been scheduled. The gaps in care item 732B is displayed in both the new items window 460 and the scheduled appointments window 462. For example, the gaps in care item 732B displayed in the new items window 460 includes a link (e.g., with the wording "SCHEDULED") to the same gaps in care item 732B displayed in the scheduled appointments window 462. The link, when selected, may provide information on a time and/or location when the appointment for the gaps in care item 732B has been scheduled. Thus, the user may readily access such information so that an appointment for the gaps in care item 732A may be scheduled near or at the same time and/or location as the appointment for the gaps in care item 732B.

Example Process Flow

Figure 8:
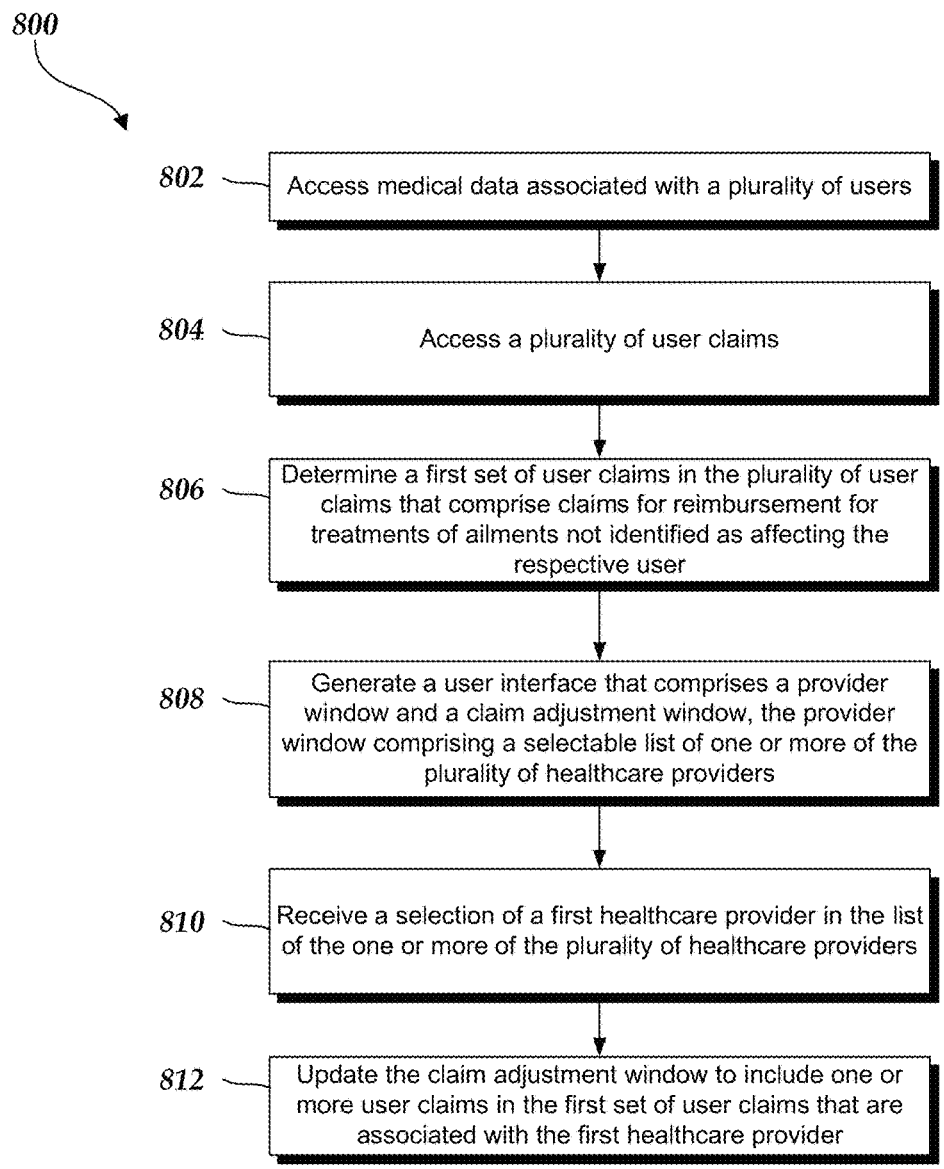
FIG. 8 is a flowchart depicting an illustrative operation of displaying claims adjustments.

FIG. 8 is a flowchart 800 depicting an illustrative operation of displaying claims adjustments. Depending on the embodiment, the method of FIG. 8 may be performed by various computing devices, such as by the insurer device 130 and/or the prescription and medical claims data server 140. For ease of discussion, the method is discussed herein with reference to insurer device 130 and the provider portal 135 of the insurer device 130. Depending on the embodiment, the method of FIG. 8 may include fewer and/or additional blocks and the blocks may be performed in an order different than illustrated.

In block 802, medical data associated with a plurality of users is accessed. For example, the medical data may include diagnosis data for a plurality of patients (e.g., ailments or conditions that a patient is diagnosed with). The medical data may be accessed from the providers 110 and/or the prescription and medical claims data server 140 and provided to the insurer device 130.

In block 804, a plurality of user claims are accessed. In an embodiment, the user claims are prescription claims and/or medical claims. In a further embodiment, the plurality of user claims are each associated with a healthcare provider in a plurality of healthcare providers.

In block 806, a first set of user claims in the plurality of user claims that comprise claims for reimbursement for treatments of ailments not identified as affecting the respective user is determined. In an embodiment, the determination is made based on comparing the received medical data with claims received on behalf of each respective patient.

In block 808, a user interface is generated that comprises a provider window and a claim adjustment window. In an embodiment, the provider window comprises a selectable list of one or more of the plurality of healthcare providers.

In block 810, a selection of a first healthcare provider in the list of the one or more of the plurality of healthcare providers is received. In block 812, the claim adjustment window is updated to include one or more user claims in the first set of user claims that are associated with the first healthcare provider.

Implementation Mechanisms

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 9:
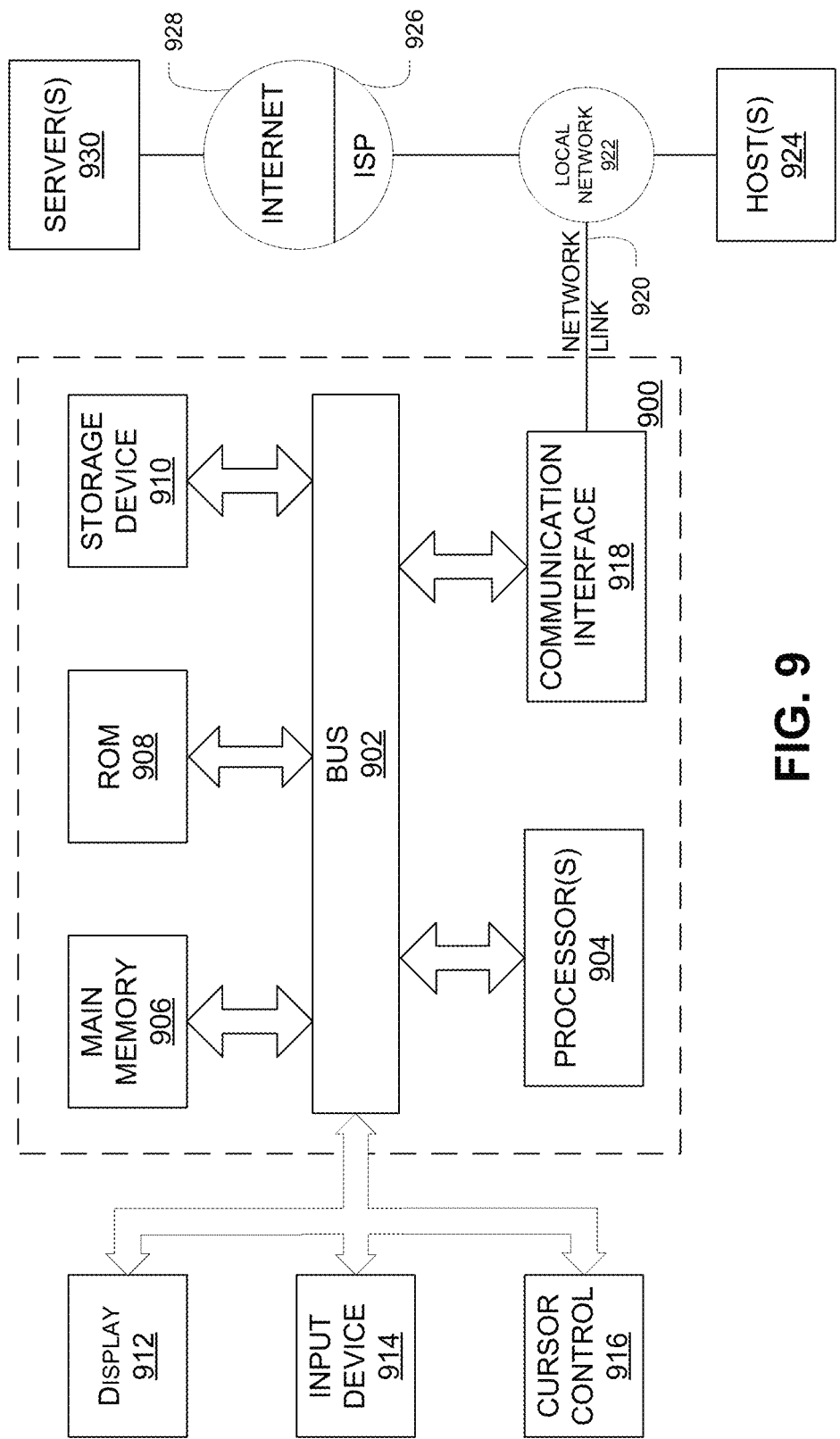
FIG. 9 illustrates a computer system with which certain methods discussed herein may be implemented.

For example, FIG. 9 is a block diagram that illustrates a computer system 900 upon which an embodiment may be implemented. For example, any of the computing devices discussed herein, such as the insurer device 130, the prescription and medical claims data server 140, the providers 110, and the patient 150 may include some or all of the components and/or functionality of the computer system 900.

Computer system 900 includes a bus 902 or other communication mechanism for communicating information, and a hardware processor, or multiple processors, 904 coupled with bus 902 for processing information. Hardware processor(s) 904 may be, for example, one or more general purpose microprocessors.

Computer system 900 also includes a main memory 906, such as a random access memory (RAM), cache and/or other dynamic storage devices, coupled to bus 902 for storing information and instructions to be executed by processor 904. Main memory 906 also may be used for storing temporary variables or other intermediate information during execution of instructions to be executed by processor 904. Such instructions, when stored in storage media accessible to processor 904, render computer system 900 into a special-purpose machine that is customized to perform the operations specified in the instructions.

Computer system 900 further includes a read only memory (ROM) 908 or other static storage device coupled to bus 902 for storing static information and instructions for processor 904. A storage device 910, such as a magnetic disk, optical disk, or USB thumb drive (Flash drive), etc., is provided and coupled to bus 902 for storing information and instructions.

Computer system 900 may be coupled via bus 902 to a display 912, such as a cathode ray tube (CRT) or LCD display (or touch screen), for displaying information to a computer user. An input device 914, including alphanumeric and other keys, is coupled to bus 902 for communicating information and command selections to processor 904. Another type of user input device is cursor control 916, such as a mouse, a trackball, or cursor direction keys for communicating direction information and command selections to processor 804 and for controlling cursor movement on display 912. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 900 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage Computer system 900 may implement the techniques described herein using customized hard-wired logic, one or more ASICs or FPGAs, firmware and/or program logic which in combination with the computer system causes or programs computer system 900 to be a special-purpose machine. According to one embodiment, the techniques herein are performed by computer system 900 in response to processor(s) 904 executing one or more sequences of one or more instructions contained in main memory 906. Such instructions may be read into main memory 906 from another storage medium, such as storage device 910. Execution of the sequences of instructions contained in main memory 906 causes processor(s) 904 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 910. Volatile media includes dynamic memory, such as main memory 906. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise bus 802. Transmission media can also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid state drive of a remote computer. The remote computer can load the instructions into its dynamic memory and send the instructions over a telephone line using a modem. A modem local to computer system 900 can receive the data on the telephone line and use an infra-red transmitter to convert the data to an infra-red signal. An infra-red detector can receive the data carried in the infra-red signal and appropriate circuitry can place the data on bus 902. Bus 902 carries the data to main memory 906, from which processor 904 retrieves and executes the instructions. The instructions received by main memory 906 may retrieve and execute the instructions. The instructions received by main memory 906 may optionally be stored on storage device 910 either before or after execution by processor 904.

Computer system 900 also includes a communication interface 918 coupled to bus 902. Communication interface 918 provides a two-way data communication coupling to a network link 920 that is connected to a local network 922. For example, communication interface 918 may be an integrated services digital network (ISDN) card, cable modem, satellite modem, or a modem to provide a data communication connection to a corresponding type of telephone line. As another example, communication interface 918 may be a local area network (LAN) card to provide a data communication connection to a compatible LAN (or WAN component to communicated with a WAN). Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to a host computer 924 or to data equipment operated by an Internet Service Provider (ISP) 926. ISP 926 in turn provides data communication services through the world wide packet data communication network now commonly referred to as the "Internet" 928. Local network 922 and Internet 928 both use electrical, electromagnetic or optical signals that carry digital data streams. The signals through the various networks and the signals on network link 920 and through communication interface 918, which carry the digital data to and from computer system 900, are example forms of transmission media.

Computer system 900 can send messages and receive data, including program code, through the network(s), network link 920 and communication interface 918. In the Internet example, a server 930 might transmit a requested code for an application program through Internet 928, ISP 926, local network 922 and communication interface 918.

The received code may be executed by processor 904 as it is received, and/or stored in storage device 910, or other non-volatile storage for later execution.

Terminology

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A system comprising:
   a computer processor; and
   a computer readable storage medium storing a plurality of program instructions configured for execution by the computer processor, wherein the plurality of program instructions, when executed, cause the computing system to:
   access a plurality of health claims associated with an entity;
   determine a first set of health claims in the plurality of health claims and a second set of health claims in the plurality of health claims;
   cause a user interface to be rendered, the user interface comprising a first window, a second window, and an interactive element, wherein the first window depicts the entity, wherein the first window further depicts a first stacked bar graph associated with the entity, wherein the first stacked bar graph comprises a first box and a second box, wherein a width of the first box is based on a number of health claims in the first set of health claims, and wherein a width of the second box is based on a number of health claims in the second set of health claims;
   receive a selection of the entity;
   in response to the selection of the entity, cause one or more health claims in the first set of health claims to be displayed in the second window;
   receive an indication of a selection of a first health claim in the one or more health claims in the first set of health claims;
   in response to reception of the indication of the selection of the first health claim,
      no longer display, in the second window, the first health claim, and
      cause the width of the first box of the first stacked bar graph to decrease from a first width to a second width less than the first width to reflect a reduced number of health claims in the first set of health claims; and
   in response to a selection of the interactive element, initiate a communication between the system and a physical computing device associated with a user.

2. The system of claim 1, wherein the program instructions are further configured to cause the computing system to identify a first set of users that have not submitted, during a first period of time, a second health claim in the plurality of health claims for reimbursement for a treatment of an ailment identified as affecting the respective user, wherein the user interface is further configured to display, in a third window, for each user in the first set of users that is associated with the entity, a notification to contact the respective user.

3. The system of claim 2, wherein the program instructions are further configured to cause the computing system to receive a selection of a first notification to contact a first user in the first set of users, wherein the user interface is further configured to display, in the third window, a schedule window that overlaps at least a portion of the first notification, wherein the schedule window comprises an option to indicate that an appointment has been scheduled with the first user and an option to indicate that the appointment with the first user has been completed.

4. The system of claim 3, wherein the third window comprises a new window and a scheduled appointment window, wherein the new window comprises the first notification, and wherein the user interface is further configured to display, in the scheduled appointment window and not the new window, the first notification in connection with a selection of the option to indicate that the appointment has been scheduled with the first user.

5. The system of claim 2, wherein the third window comprises a first notification to contact a first user in the first set of users and a notification number associated with the first notification that indicates a reason to contact the first user.

6. The system of claim 5, wherein the user interface is further configured to display, in the third window, a second notification to contact the first user and a third notification to contact the first user in connection with a selection of the first notification.

7. The system of claim 1, wherein the first stacked bar graph comprises information displayed using a logarithmic scale.

8. The system of claim 1, wherein the user interface comprises a sort button, and wherein the sort button, when selected, causes the second window to display the one or more health claims in the first set of health claims in one of an alphabetical order, an order based on date, or an order based on importance of the respective medical claim.

9. The system of claim 1, wherein health claims in the first set of claims that are associated with a first user comprise health claims for reimbursement for treatment of a first ailment, and wherein the first ailment is not identified by the entity as affecting the first user.

10. A computer-implemented method comprising:
   as implemented by one or more computer systems comprising a computer processor and main memory, the one or more computer systems configured with specific executable instructions,
   accessing a plurality of health claims associated with an entity;
   determining a first set of health claims in the plurality of health claims and a second set of health claims in the plurality of health claims;
   causing a user interface to be rendered, the user interface comprising a first window, a second window, and an interactive element, wherein the first window depicts the entity, wherein the first window further depicts a first stacked bar graph associated with the entity, wherein the first stacked bar graph comprises a first box and a second box, and wherein a width of the first box is based on a number of health claims in the first set of health claims, and wherein a width of the second box is based on a number of health claims in the second set of health claims;

receiving a selection of the entity;

in response to the selection of the entity, causing one or more health claims in the first set of health claims to be displayed in the second window;

receive an indication of a selection of a first health claim in the one or more health claims in the first set of health claims;

in response to reception of the indication of the selection of the first health claim, no longer display, in the second window, the first health claim, and cause the width of the first box of the first stacked bar graph to decrease from a first width to a second width less than the first width to reflect a reduced number of health claims in the first set of health claims; and in response to a selection of the interactive element, initiating a communication between the one or more computer systems and a physical computing device associated with a user.

11. The method of claim 10, further comprising:

identifying a first set of users that have not submitted, during a first period of time, a second health claim in the plurality of health claims for reimbursement for a treatment of an ailment identified as affecting the respective user; and updating a third window in the user interface, for each user in the first set of users that is associated with the entity, to include a notification to contact the respective user.

12. The method of claim 10, wherein health claims in the first set of health claims that are associated with a first user comprise health claims for reimbursement for treatment of a first ailment, and wherein the first ailment is not identified by the entity as affecting the first user.

13. The method of claim 10, wherein the first stacked bar graph comprises information displayed using a logarithmic scale.

14. The method of claim 10, further comprising receiving a selection of a first notification to contact a first user, wherein the user interface is further configured to display a schedule window that overlaps at least a portion of the first notification, and wherein the user interface comprises an option to indicate that an appointment has been scheduled with the first user and an option to indicate that the appointment with the first user has been completed.

15. The method of claim 14, wherein the user interface is further configured to display a new window and a scheduled appointment window, wherein the new window comprises the first notification, and wherein the user interface is further configured to display, in the scheduled appointment window and not the new window, the first notification in connection with a selection of the option to indicate that the appointment has been scheduled with the first user.

16. A non-transitory computer-readable medium comprising one or more program instructions recorded thereon, the instructions configured for execution by a computing system comprising one or more processors in order to cause the computing system to:

access a plurality of health claims associated with a first entity;

determine a first set of health claims in the plurality of health claims and a second set of health claims in the plurality of health claims;

cause a user interface to be rendered, the user interface comprising a first window, a second window, and an interactive element, wherein the first window depicts the entity, wherein the first window further depicts a first stacked bar graph associated with the entity, wherein the first stacked bar graph comprises a first box and a second box, wherein a width of the first box is based on a number of health claims in the first set of health claims, and wherein a width of the second box is based on a number of health claims in the second set of health claims;

receive a selection of the entity;

in response to the selection of the entity, cause one or more health claims in the first set of health claims to be displayed in the second window;

receive an indication of a selection of a first health claim in the one or more health claims;

in response to reception of the indication of the selection of the first health claim, no longer display, in the second window, the first health claim, and cause the width of the first box of the first stacked bar graph to decrease from a first width to a second width less than the first width to reflect a reduced number of health claims in the first set of health claims; and in response to a selection of the interactive element, initiate a communication between the computing system and a physical computing device associated with a user.

17. The medium of claim 16, wherein the instructions are further configured to cause the computing system to:

identify a first set of users that have not submitted, during a first period of time, a second health claim in the plurality of health claims for reimbursement for a treatment of an ailment identified as affecting the respective user; and update the user interface, for each user in the first set of users that is associated with the entity, to include a notification to contact the respective user.

18. The medium of claim 16, wherein health claims in the first set of health claims that are associated with a first user comprise health claims for reimbursement for treatment of a first ailment, and wherein the first ailment is not identified by the entity as affecting the first user.

19. The medium of claim 16, wherein the first stacked bar graph comprises information displayed using a logarithmic scale.

20. The medium of claim 17, wherein the updated user interface comprises a first notification to contact a first user in the first set of users and a notification number associated with the first notification that indicates a reason to contact the first user.

* * * * *